United States Patent [19]
Migita et al.

[11] Patent Number: 5,454,019
[45] Date of Patent: Sep. 26, 1995

[54] COMPUTED TOMOGRAPHY SYSTEM

[75] Inventors: Shinichi Migita, Ryugasaki; Osamu Miyazaki, Ibaraki; Testuo Nakazawa, Nagareyama, all of Japan

[73] Assignee: Hitachi, Ltd., Tokyo, Japan

[21] Appl. No.: 851,930

[22] Filed: Mar. 16, 1992

[30] Foreign Application Priority Data

Mar. 15, 1991 [JP] Japan ................... 3-076954
Mar. 15, 1991 [JP] Japan ................... 3-076956

[51] Int. Cl.⁶ ........................... A61B 6/03; G01N 23/083
[52] U.S. Cl. ................... 378/15; 378/16; 378/901
[58] Field of Search ................... 378/901, 14, 4, 378/15, 16

[56] References Cited

U.S. PATENT DOCUMENTS

| | | | |
|---|---|---|---|
| 4,630,202 | 12/1986 | Mori | 364/414 |
| 5,046,003 | 9/1991 | Crawford | 364/413.15 |
| 5,170,346 | 12/1992 | Crawford et al. | 364/413.16 |
| 5,208,746 | 5/1993 | King et al. | 364/413.16 |
| 5,212,717 | 5/1993 | Hada | 378/4 |
| 5,216,601 | 6/1993 | Crawford et al. | 364/413.16 |
| 5,218,623 | 6/1993 | Toki et al. | 378/4 |
| 5,233,518 | 8/1993 | King et al. | 364/413.18 |
| 5,270,923 | 12/1993 | King et al. | 364/413.13 |

*Primary Examiner*—David P. Porta
*Assistant Examiner*—David Vernon Bruce
*Attorney, Agent, or Firm*—Antonelli, Terry, Stout & Kraus

[57] ABSTRACT

A computed tomography system includes an image reconstruction data generator for generating image reconstruction data for a desired slice plane of an object in accordance with measuring projection data, the image reconstruction data being obtained from measuring projection data obtained at each of a plurality of rotation positions of a radiation source, and an image reconstructor for obtaining tomographic image data of the object for the desired slice plane in accordance with the image reconstruction data. The image reconstruction data generator has the capability of grouping the measuring projection data into a plurality of groups respectively corresponding to a plurality of desired slice planes of the object, the desired slice planes being spaced apart from each other by a distance corresponding to one rotation position of the radiation source, with each of the groups corresponding to a continuous rotation range of 360° of the radiation source, and successively using the measuring projection data of each group for the image reconstruction data.

7 Claims, 15 Drawing Sheets

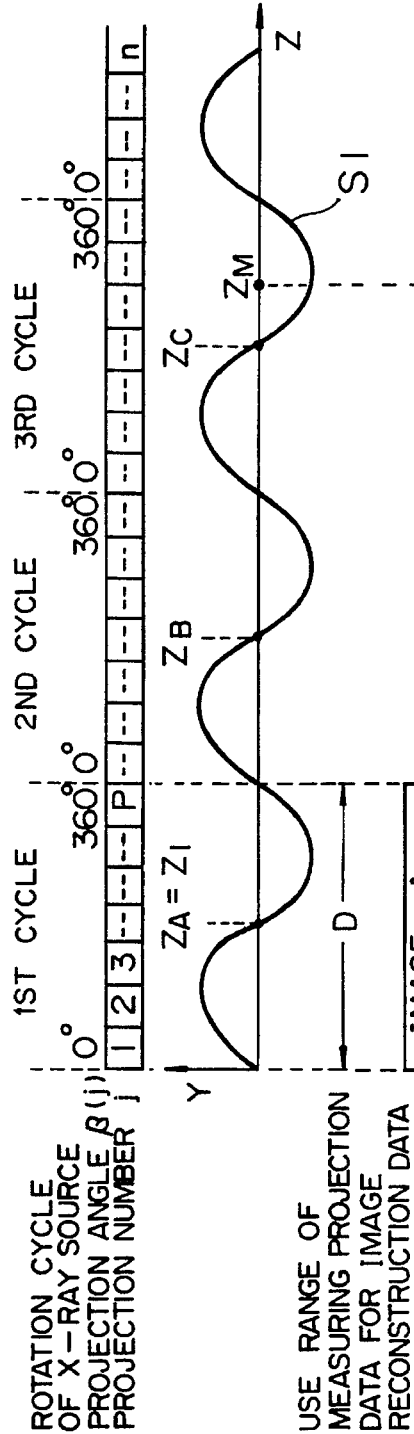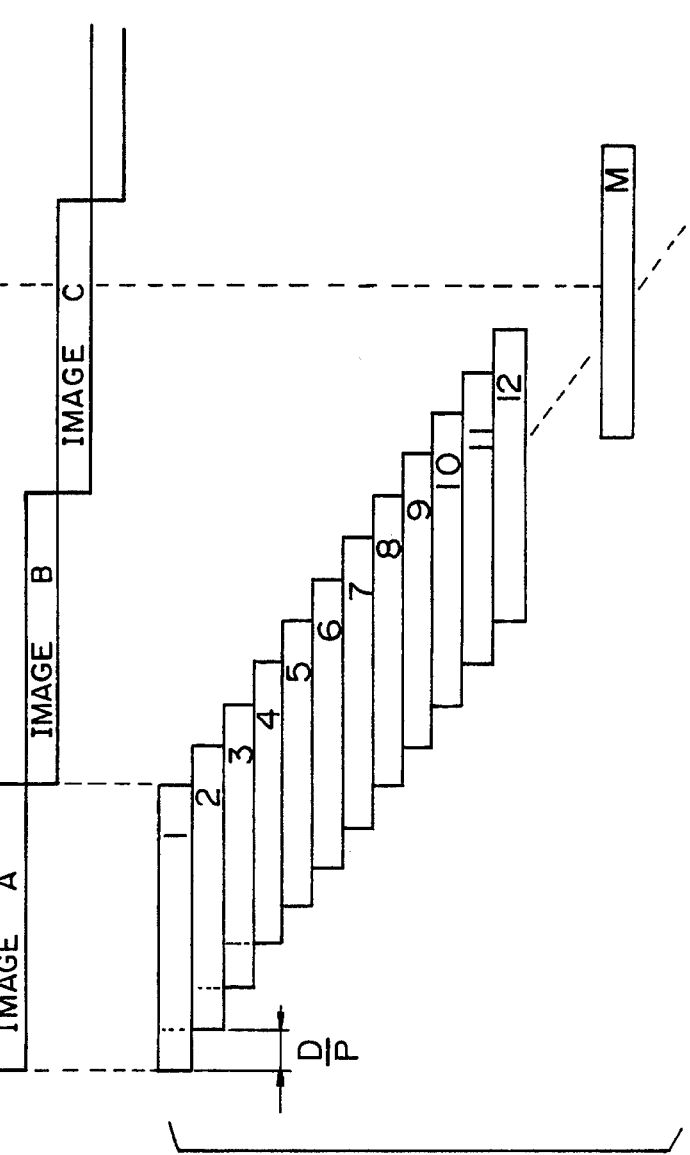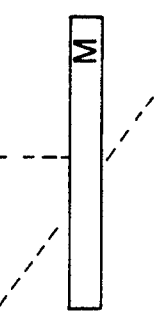
FIG. 8A ROTATION CYCLE OF X-RAY SOURCE PROJECTION ANGLE β(j) PROJECTION NUMBER j
FIG. 8B USE RANGE OF MEASURING PROJECTION DATA FOR IMAGE RECONSTRUCTION DATA
FIG. 8C
FIG. 8D USE RANGE OF MEASURING PROJECTION DATA FOR IMAGE RECONSTRUCTION DATA

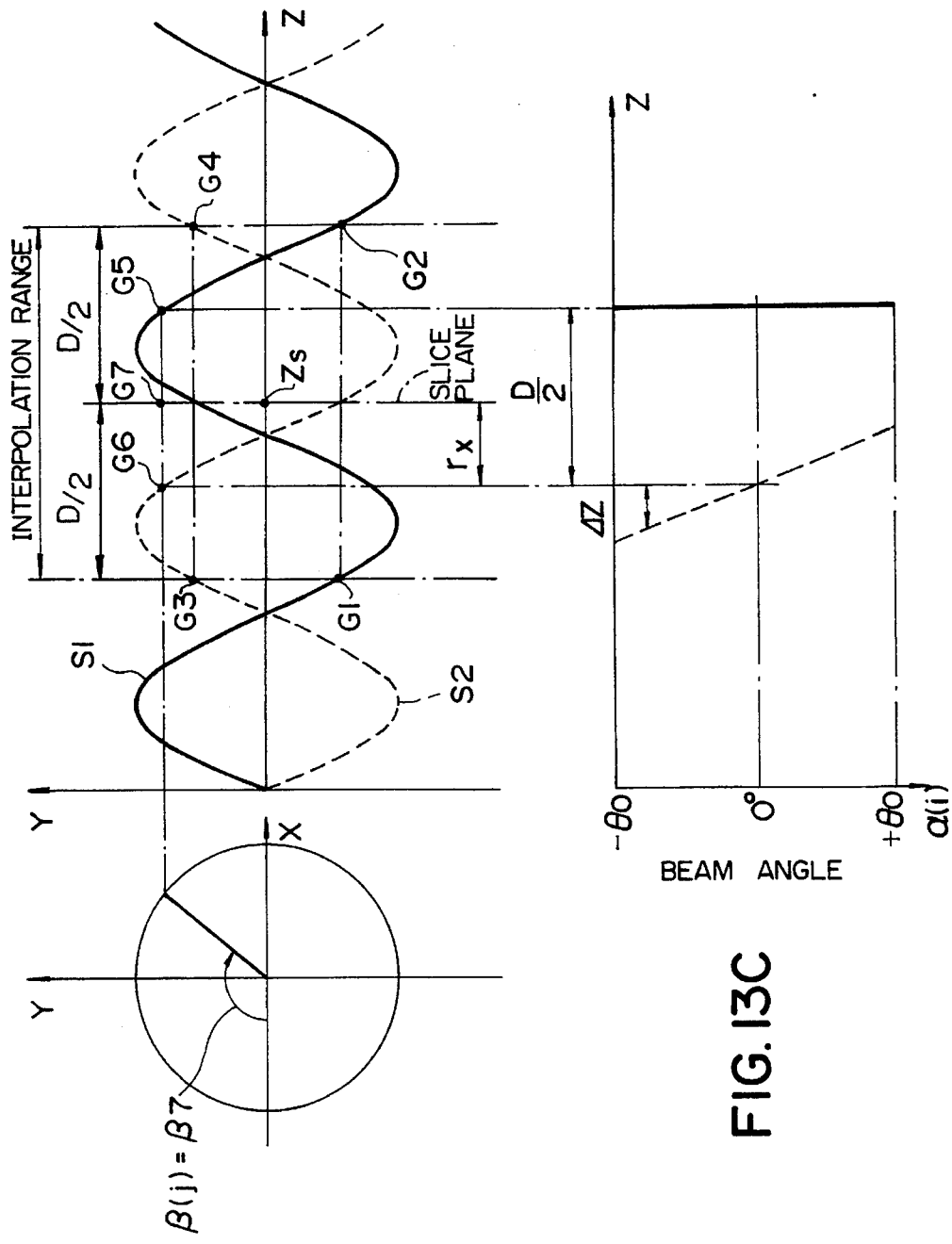

CONTRIBUTION FACTOR (%) OF MEASURING PROJECTION DATA

CONTRIBUTION FACTOR (%) OF MEASURING PROJECTION DATA

CONTRIBUTION FACTOR (%) OF MEASURING PROJECTION DATA

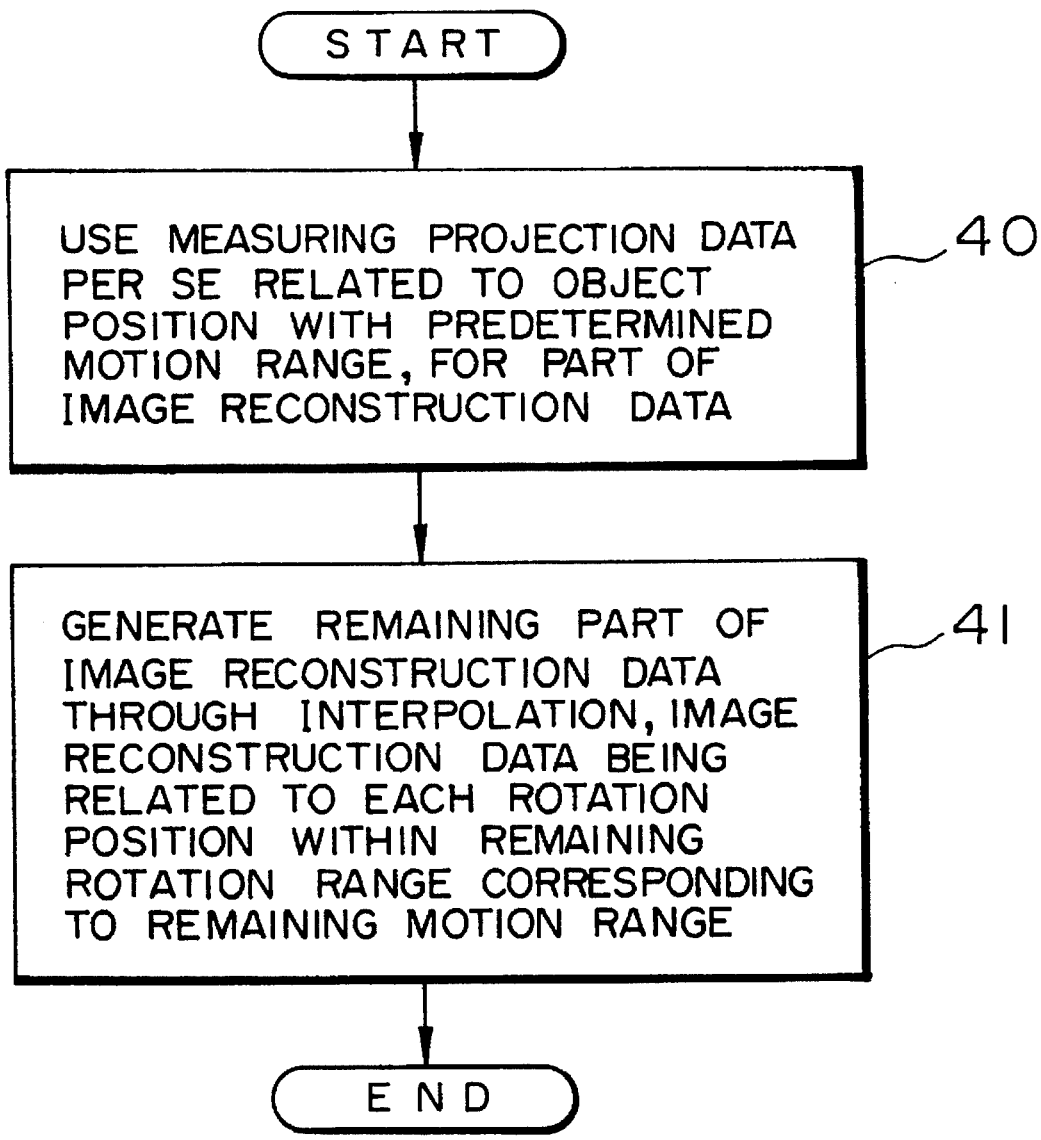

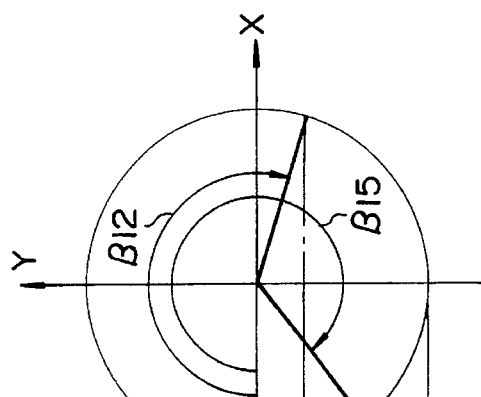
FIG.16B
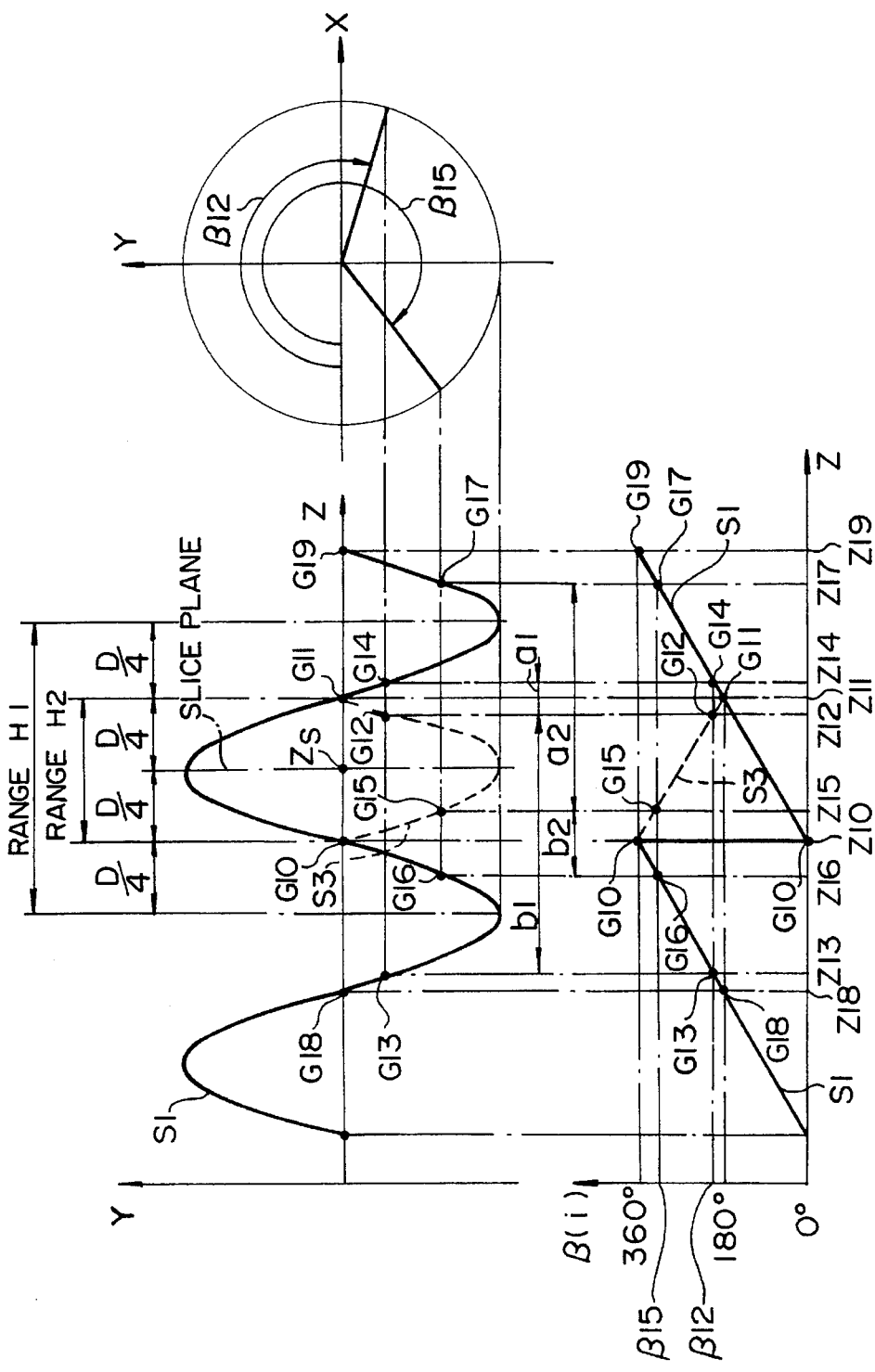
FIG.16A
FIG.16C

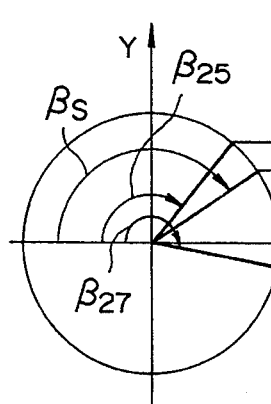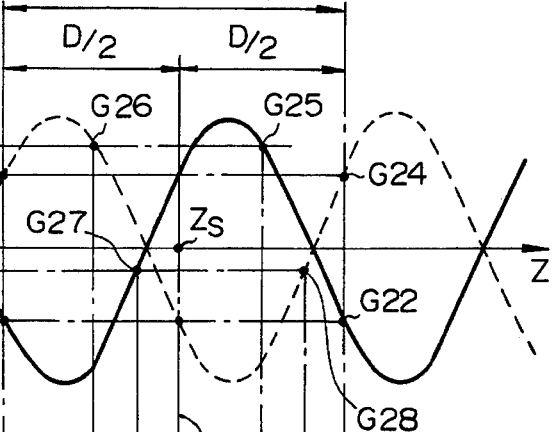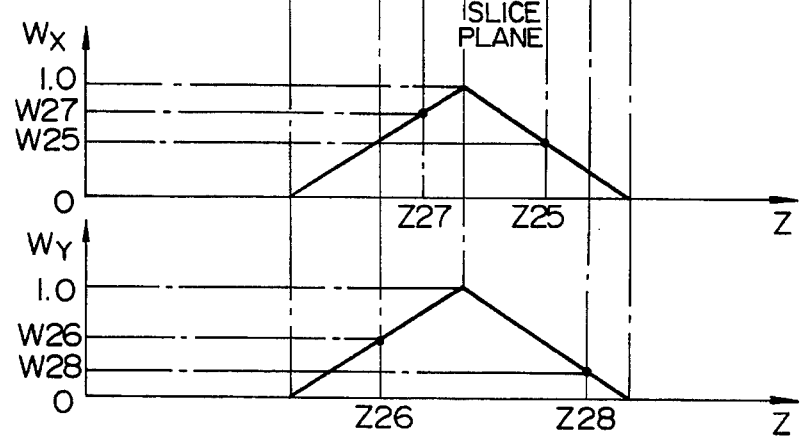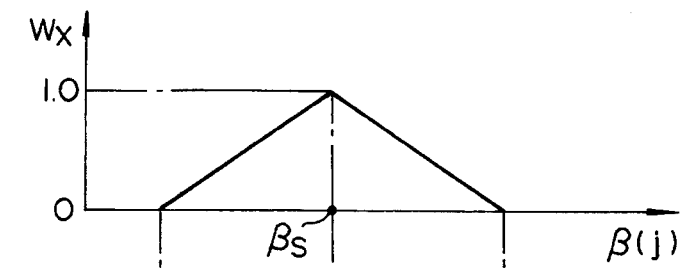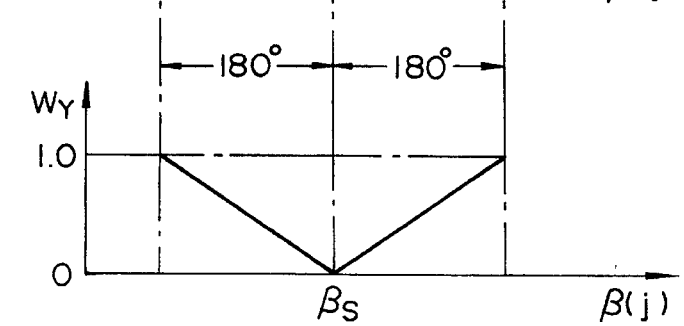

COMPUTED TOMOGRAPHY SYSTEM

BACKGROUND OF THE INVENTION

The present invention relates to a computed tomography (CT) system. Specifically, the present invention relates to a CT system in which a radiation source such as an X-ray source irradiates radiation rays to an object such as a patient while spirally moving the radiation source relative to the object, the radiation rays transmitted through the object are detected with a detector, measuring projection data is obtained from the signal detected with the detector, and tomographic image data of the object is obtained from the measuring projection data.

With a conventional CT system, a tomogram at a desired slice plane of an object, e.g., patient, is taken in the following manner. X-rays are irradiated from an X-ray source to a stationary patient while rotating the X-ray source about the patient in the vertical plane containing the slice plane. Projection data from a plurality of directions at the slice plane is collected, and a tomographic image is reconstructed using the projection data. For the convenience of description, such projection data is called stationary patient (object) projection data.

If a plurality of tomograms at a plurality of different slice planes of a patient are to be obtained using such a conventional CT system, the following operations become necessary. After collecting projection data while rotating an X-ray source within one slice plane, the X-ray source temporarily stops its operation. During this stop period, the patient is moved horizontally to enable the X-ray source to be positioned within the vertical plane containing the next slice plane. Then, projection data for this slice plane is collected. The conventional CT system requires such operations, resulting in a long period of restricting the patient and a poor work efficiency of the system.

To eliminate such disadvantages, a CT system providing spiral scanning has been proposed. Such CT systems are disclosed in U.S. Pat. No. 4,630,202 corresponding to JP-A-59-111738, and U.S. Pat. No. 4,789,929 corresponding to JP-A-62-87137 and JP-A-62-139630.

CT systems disclosed in U.S. Pat. Nos. 4,630,202 and 4,789,929 process measuring projection data obtained through spiral scanning by the methods specific to the systems, and obtain data corresponding to the stationary patient projection data. The obtained data is assumed to be the stationary patient projection data, and a tomographic image is reconstructed in the manner similar to a conventional CT system of a stationary patient type.

SUMMARY OF THE INVENTION

It is an object of the present invention to provide a CT system performing spiral scanning in which measuring projection data obtained through spiral scanning is processed in a manner different from that of a conventional CT system.

It is another object of the present invention to provide a CT system performing spiral scanning capable of obtaining tomographic image data at a desired slice plane of an object.

It is a further object of the present invention to provide a CT system performing spiral scanning capable of obtaining tomographic image data of high precision.

It is a still further object of the present invention to provide a CT system performing spiral scanning capable of reducing image artifacts.

According to one aspect of the present invention, the above objects can be achieved through provision of a CT system including a radiation source for irradiating a fan beam radiation ray to an object, the radiation source continuously rotating within a predetermined rotation plane, and the fan beam radiation ray expanding in a fan shape substantially within the rotation plane; a motion unit for continuously moving the object in a predetermined direction such that the rotation plane continuously traverses different parts of the object while the radiation source rotates; a radiation detector mounted on the opposite side of the object relative to the radiation source, the radiation detector including a plurality of detector elements disposed so as to receive radiation of the fan beam radiation ray, each detector element being responsive to a radiation beam which is part of the fan beam radiation ray transmitted through the object and outputting a measuring projection signal corresponding to the intensity of the radiation beam; a data collecting unit for collecting measuring projection data for each radiation beam at each of a plurality of predetermined rotation positions of the radiation source in accordance with the measuring projection signal while relating each measuring projection data to the rotation position of the radiation source, the position of the object moved by the motion unit, and the position of the radiation beam of the fan beam radiation ray; an image reconstruction data generator for generating image reconstruction data at a predetermined slice plane of the object in accordance with the measuring projection data, the image reconstruction data being obtained from the measuring projection data obtained at each rotation position of the radiation source; and an image reconstruction unit for obtaining tomographic image data of the object at the predetermined slice plane in accordance with the image reconstruction data. The image reconstruction data generator includes a unit for dividing the measuring projection data into groups each falling within a continuous rotation range of 360° of the radiation source, and for using the measuring projection data of each group for the image reconstruction data.

With this CT system, the measuring projection data per se is used for the image reconstruction data. Therefore, although artifacts are relatively large, the processing by the image reconstruction data generator is simple and can be executed at a high speed.

According to another aspect of the present invention, the CT system includes, similar to the CT system described above, the radiation source, the motion unit, the radiation detector, the data collecting unit, the image reconstruction data generator, and the image reconstruction unit. In this CT system, the image reconstruction data generator includes a selector unit for selecting the measuring projection data at a rotation position within a predetermined continuous rotation range of the radiation source necessary for image reconstruction, and for using the selected measuring projection data for the image reconstruction data, the predetermined continuous rotation range being shifted in accordance with the position of a desired slice plane of the object.

With this CT system, similar to the CT system of the first aspect, not only the processing by the image reconstruction data generator is simple and can be executed at a high speed, but also tomographic image data can be obtained at any desired slice plane of an object.

According to a further aspect of the present invention, provided is a CT system including a radiation source for irradiating a fan beam radiation ray to an object, the radiation source continuously rotating within a predetermined rotation plane, and the fan beam radiation ray expanding in a fan shape substantially within the rotation plane; a motion unit for continuously moving the object in a predetermined direction such that the rotation plane continuously traverses different parts of the object while the radiation source rotates; a radiation detector mounted on the opposite side of the object relative to the radiation source, the radiation detector including a plurality of detector elements disposed so as to receive radiation of the fan beam radiation ray, each detector element being responsive to a radiation beam which is part of the fan beam radiation ray transmitted through the object and outputting a measuring projection signal corresponding to the intensity of the radiation beam; a data collecting unit for collecting measuring projection data for each radiation beam at each of a plurality of predetermined rotation positions of the radiation source in accordance with the measuring projection signal while relating each measuring projection data to the rotation position of the radiation source, the position of the object moved by the motion unit, and the position of the radiation beam of the fan beam radiation ray; an image reconstruction data generator for generating image reconstruction data at a predetermined slice plane of the object in accordance with the measuring projection data, the image reconstruction data being obtained from the measuring projection data obtained at each rotation position of the radiation source; and an image reconstruction unit for obtaining tomographic image data of the object at the predetermined slice plane in accordance with the image reconstruction data. The image reconstruction data generator includes a counter projection data generator for generating counter projection data for each measuring projection data, the counter projection data being substantially the same as a corresponding one of the measuring projection data and being related to the rotation position of the radiation source, the position of the object moved by the motion unit, and the position of a virtual radiation beam of the fan beam radiation ray, the virtual radiation beam having substantially the same path as, and a direction opposite to, the radiation beam for the corresponding one of the measuring projection data; and a data generator for obtaining the image reconstruction data in accordance with the measuring projection data and the counter projection data.

With this CT system, the image reconstruction data can be obtained from the measuring projection data substantially the same as would be obtained at a desired slice plane of the object at each rotation position of the radiation source, i.e., the same as would be obtained from a stationary object. Therefore, artifacts can be made small. Furthermore, with this CT system, not only the measuring projection data but also the counter projection data is used, making it possible to obtain tomographic image data of high precision.

According to a still further aspect of the present invention, provided is a CT system including a radiation source for irradiating a fan beam radiation ray to an object, the radiation source continuously rotating within a predetermined rotation plane, and the fan beam radiation ray expanding in a fan shape substantially within the rotation plane; a motion unit for continuously moving the object in a predetermined direction such that the rotation plane continuously traverses different parts of the object while the radiation source rotates; a radiation detector mounted on the opposite side of the object relative to the radiation source, the radiation detector including a plurality of detector elements disposed so as to receive radiation of the fan beam radiation ray, each detector element being responsive to a radiation beam which is part of the fan beam radiation ray transmitted through the object and outputting a measuring projection signal corresponding to the intensity of the radiation beam; a data collecting unit for collecting measuring projection data for each radiation beam at each of a plurality of predetermined rotation positions of the radiation source in accordance with the measuring projection signal while relating each measuring projection data to the rotation position of the radiation source, the position of the object moved by the motion unit, and the position of the radiation beam of the fan beam radiation ray; an image reconstruction data generator for generating image reconstruction data at a predetermined slice plane of the object in accordance with the measuring projection data, the image reconstruction data being substantially the same data as measuring projection data obtained while smoothly moving the object so as to move the rotation plane from the anterior position of a slice area of the object to the posterior position and to return to substantially the original position during one rotation of the radiation source; and an image reconstruction unit for obtaining tomographic image data of the object at the predetermined slice plane in accordance with the image reconstruction data.

With this CT system, the image reconstruction data generator generates image reconstruction data as if the object were moved in the manner described above. Therefore, the difference between image reconstruction data at adjacent rotation positions can be made small, thus reducing artifacts.

BRIEF DESCRIPTION OF THE DRAWINGS

FIG. 8A shows the relation between rotation cycles of the X-ray source and projection numbers, FIG. 8B shows the locus of the X-ray source relative to a patient in association with projection numbers, FIG. 8C shows an example of the use range of the measuring projection data for the image reconstruction data in association with projection numbers, and FIG. 8D shows another example of the use range of the measuring projection data for the image reconstruction data in association with projection numbers.

FIG. 13A shows an actual locus of the X-ray source and a virtual locus of the X-ray source of the counter projection data, FIG. 13B shows the relation between each locus and a projection angle, and FIG. 13C shows the relation between the beam angle for the measuring projection data at a certain projection angle and the bed position, and the relation between the beam angle for the counter projection data at the projection angle and the bed position.

FIG. 15 is a flow chart showing the function of the image reconstruction data generator of the CT system according to a still further embodiment of the present invention.

FIG. 16A shows an actual locus and a virtual locus of the X-ray source, FIG. 16B shows the relation between each locus and a projection angle, and FIG. 16C also shows the relation between each locus and a projection angle.

FIG. 18A shows an actual locus of the X-ray source and a virtual locus of the X-ray source for the counter projection data, FIG. 18B shows the relation between each locus and a projection angle, FIG. 18C shows the relation between each locus and the weight coefficients for the measuring projection data, FIG. 18D shows the relation between each locus and the weight coefficients for the counter projection data, FIG. 1BE shows another representation of the weight coefficients shown in FIG. 18C, and FIG. 18F shows another representation of the weight coefficients shown in FIG. 18D.

DESCRIPTION OF THE PREFERRED EMBODIMENTS

Preferred embodiments of a computed tomography (CT) system according to the present invention will be described with reference to the accompanying drawings.

A first embodiment of the CT system of the present invention will be described while referring to FIGS. 1–4, 5A–5C, 6–7, and 8A–8D.

Figure 1:
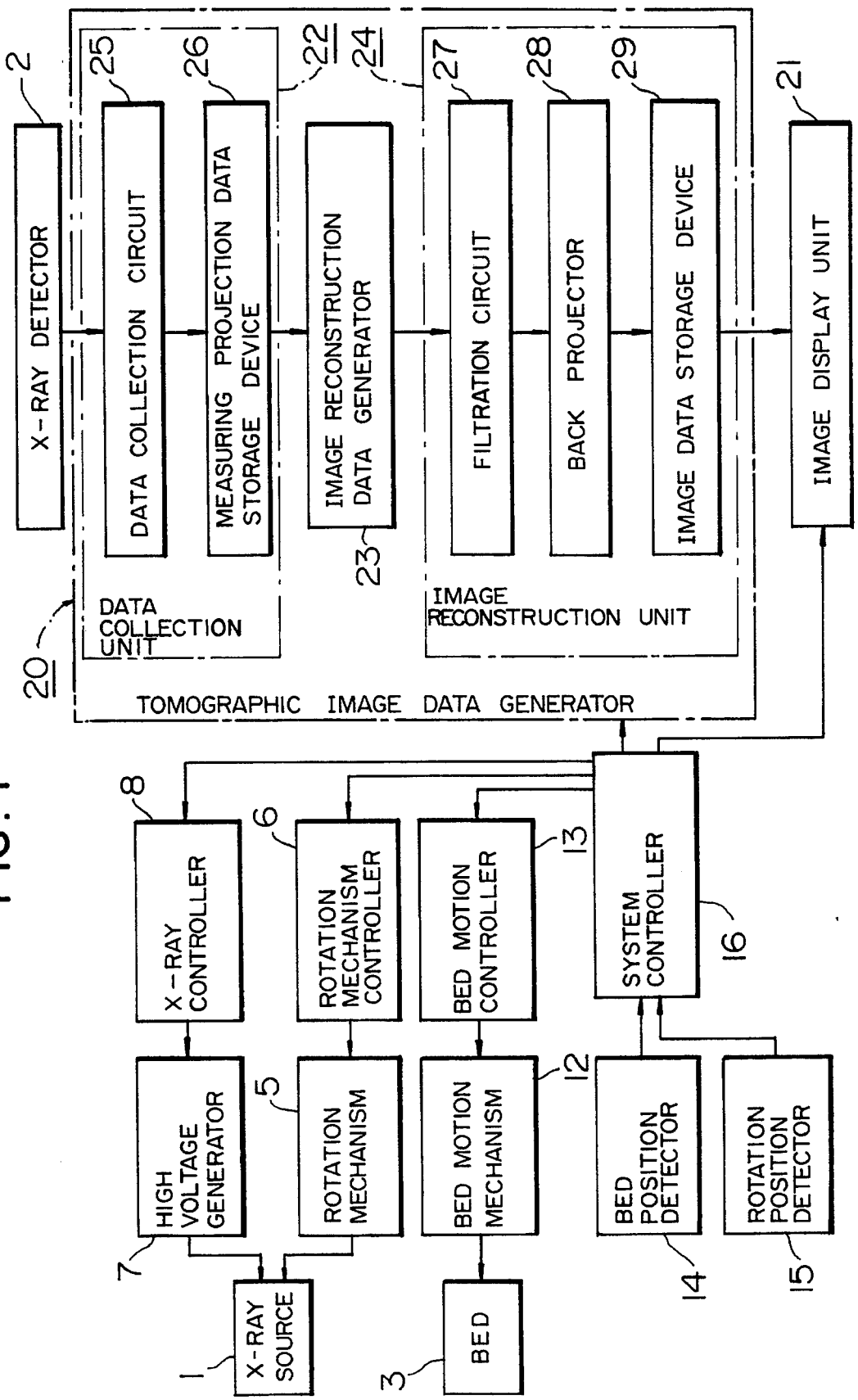
FIG. 1 is a block diagram showing an embodiment of a CT system according to the present invention.
Figure 2:
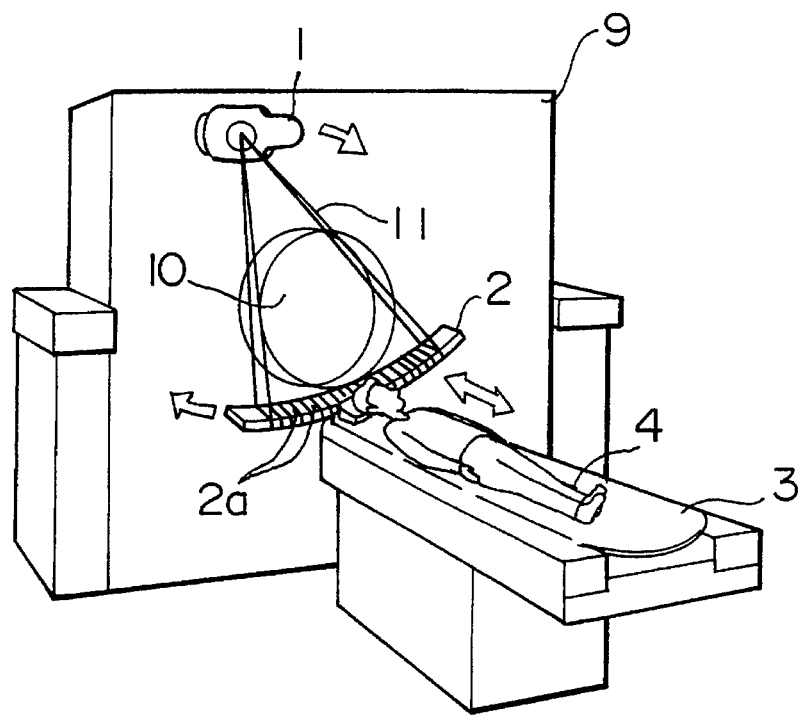
FIG. 2 is a schematic perspective view of the CT system shown in FIG. 1.

FIG. 1 is a block diagram showing the overall structure of a CT system of a rotate/rotate type according to the first embodiment of the present invention, and FIG. 2 is a schematic perspective view of the CT system shown in FIG. 1.

In FIGS. 1 and 2, reference numeral 1 represents a radiation source such as an X-ray source or X-ray tube, reference numeral 2 represents a radiation detector such as an X-ray detector, and reference numeral 3 represents a bed for placing thereon an object such as a patient 4. The X-ray source 1 is adapted to be rotatable about an aperture 10 formed in a gantry 9 and within a predetermined rotation plane (in this example, within a vertical plane) by a rotation mechanism 5. The rotation mechanism 5 is driven under the control of a rotation mechanism controller 6. The X-ray source 1 is supplied with a predetermined high voltage from a high voltage source 7, and irradiates a fan beam X-ray 11 propagating as a fan beam within the rotation plane as shown in FIG. 2. The X-ray source 1 has a function of changing the slice thickness SW of the fan beam X-ray 11 within a range of, e.g., $0 < SW \leq 20$ mm. An X-ray controller 8 controls the timing when the high voltage source 7 applies a high voltage to the X-ray source and the amplitude of the high voltage to thereby control the generation timing and amplitude of the fan beam X-ray 11. The high voltage is supplied from the high voltage source 7 to the X-ray source 1 by means of a known slip ring (not shown), allowing the X-ray source 1 to continuously and repetitively rotate. The X-ray detector 2 is disposed facing the X-ray source 1 across the gantry aperture 10. The X-ray detector 2 and X-ray source 1 are rotated by the rotation mechanism 5 while maintaining the opposing position therebetween. The X-ray source 2 has a plurality of detector elements 2a covering the area of the fan beam X-ray 11. Each detector element 2a receives an X-ray beam which is a fraction of the fan beam X-ray 11 transmitted through the patient 4, and outputs a measuring projection signal corresponding to the intensity of the received X-ray beam. In this embodiment, the positional relation between the X-ray source 1 and X-ray detector 2 is always constant, so that each X-ray beam of the fan beam X-ray 11 has a one-to-one correspondence with one particular detector element 2a. A bed motion mechanism 12 causes the bed 3 to move backward or forward in the direction perpendicular to the rotation plane of the X-ray source 1, and hence to enter or exit the gantry aperture 10. In this embodiment, the motion of the bed 3 is in a direction perpendicular to the rotation plane of the X-ray source 1. However, this motion of the bed 3 may be set in a direction oblique to the rotation plane. The bed motion mechanism 12 is driven under the control of a bed motion controller 13. In FIG. 1, reference numeral 14 represents a bed position detector for detecting the position of the bed 3, and reference numeral 15 represents a rotation position detector for detecting the rotation position of the X-ray source 1. Signals outputted from these detectors are supplied to a system controller 16.

Figure 3:
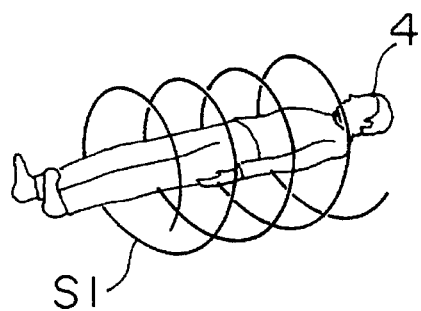
FIG. 3 is a perspective view showing an actual locus of the X-ray source relative to a patient.

In response to signals from the bed position detector 14, rotation detector 15, and a console (not shown), the system controller 16 sends control signals to the X-ray controller 8, rotation mechanism controller 6, and bed motion controller 13. The fan beam X-ray 11 is then generated continuously or intermittently while the X-ray source 1 is rotated continuously at a predetermined speed and the bed 3 is moved continuously at a predetermined speed. Therefore, the actual locus of the X-ray source 1 relative to the patient 4 is a spiral locus S1 as shown in FIG. 3, performing so-called spiral scanning. In the following description, it is assumed that the bed 3 moves by a distance D per one rotation of the X-ray source 1. In this embodiment, the rotation speed of the X-ray source 1 and the motion speed of the bed 3 are constant. However, these speeds may be changed as desired.

Figure 4:
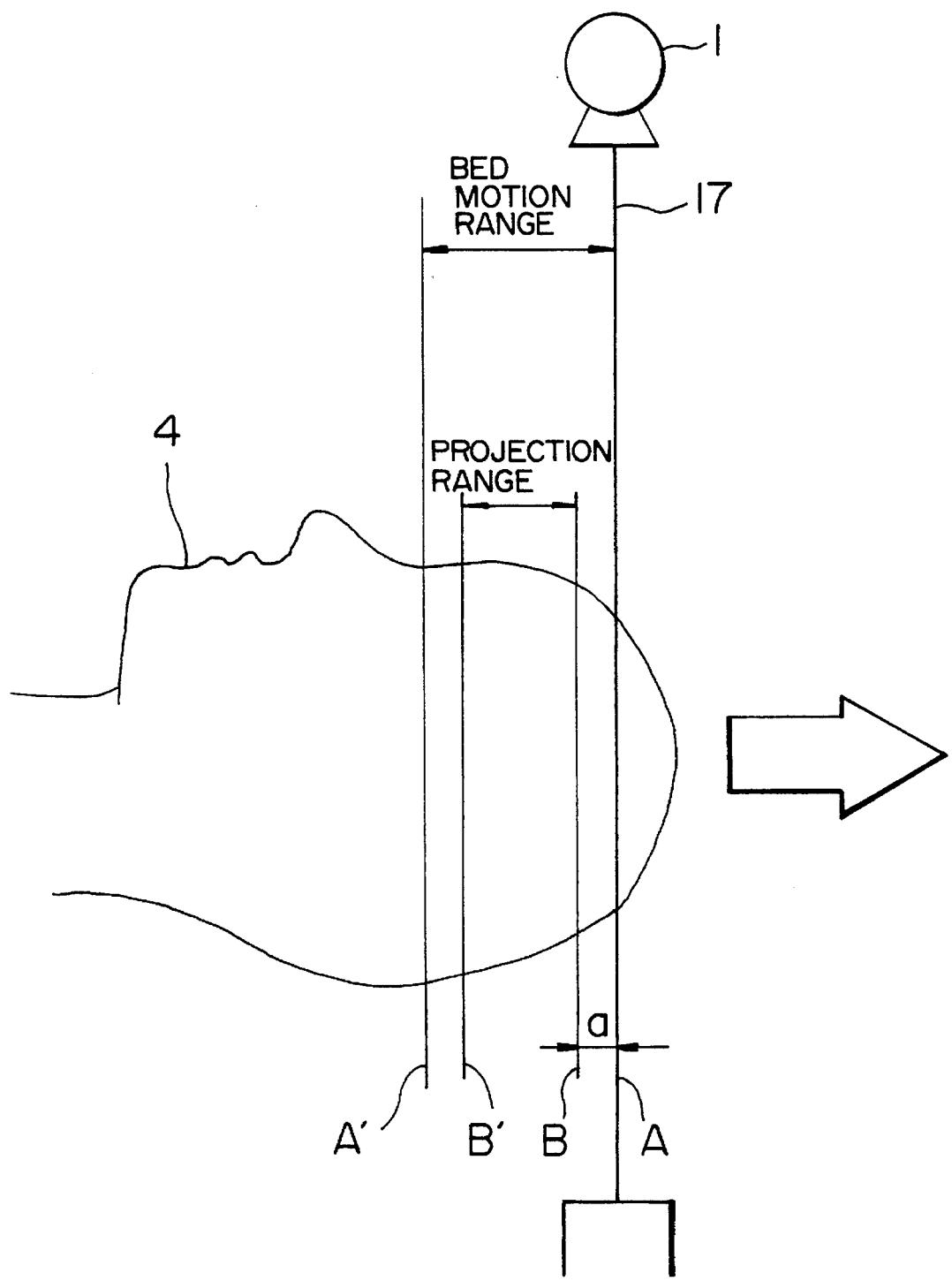
FIG. 4 is a diagram showing the relation between a patient and the projection range.
Figure 5A:
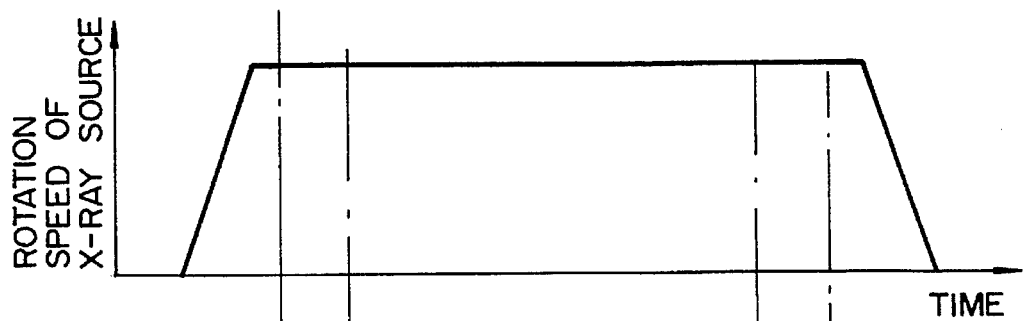
FIGS. 5A, 5B, and 5C are timing charts showing the relation between the rotation speed of the X-ray source, bed motion speed, and X-ray exposure.
Figure 5B:
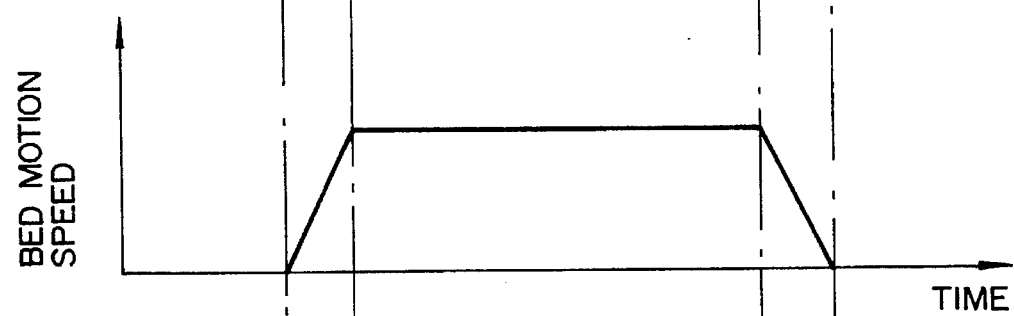
Figure 5C:
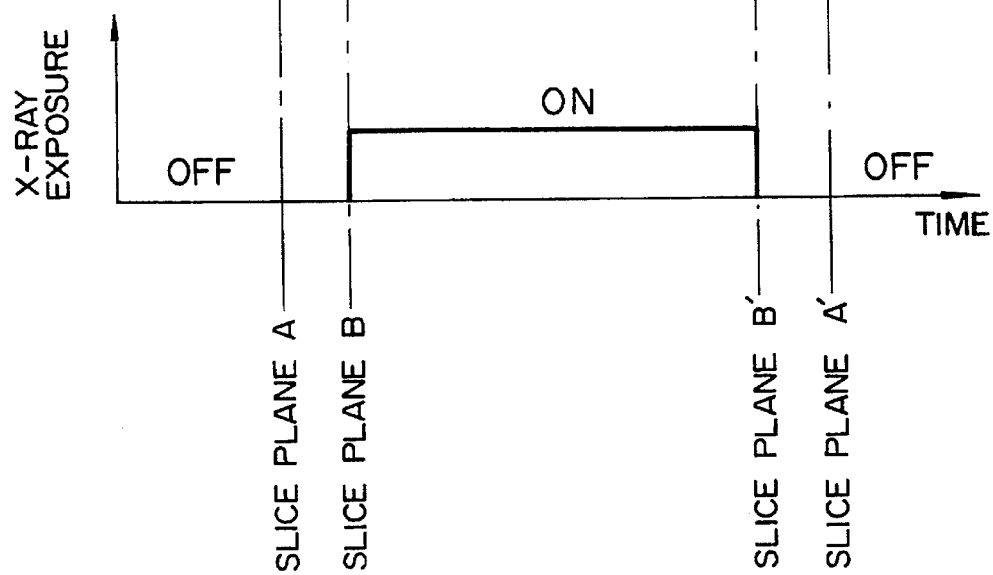

The above-described spiral scanning is carried out within an area (hereinafter called an image reconstruction area) containing slice planes from which desired tomographic images of a patient are intended to be obtained. FIG. 4 shows a relation between the position of the patient 4 and the projection area to which the fan beam X-ray 11 is irradiated during spiral scanning. FIGS. 5A, 5B, and 5C are timing charts showing a relation between the rotation speed of the X-ray source 1, the motion speed of the bed 3, and the X-ray exposure in connection with the case shown in FIG. 4. In this case, the area from a slice plane B to a slice plane B' of the patient 4 corresponds to the projection area. The projection area contains the image reconstruction area, and if necessary, it may be set wider than the image reconstruction area. Consider the case illustrated in FIGS. 4, 5A, 5B, and 5C. The bed 3 is first set to the position where a slice plane A of the patient 4 ahead of the slice plane B by a distance a aligns with the rotation plane 17 of the X-ray source 1. The distance a is set greater than the distance required for the motion speed of the bed 3 to become constant after it starts moving. After the bed 3 is set to such a position, the X-ray source 1 starts rotating and thereafter the bed 3 starts moving respectively as shown in FIGS. 5A and 5B. Then, as shown in FIG. 5C, exposure with the fan beam X-ray 11 starts when the slice plane B aligns with the rotation plane 17. Before this timing, the X-ray source 1 has attained a constant rotation speed. Thereafter, as seen from FIGS. 5B and 5C, the exposure with the fan beam X-ray 11 is stopped and the bed 3 is decelerated when the slice plane B' aligns with the rotation plane 17. The bed 3 thereafter stops when the slice plane A' of the patient 4 aligns with the rotation plane 17 as shown in FIG. 5B. Lastly, the X-ray source 1 is decelerated and it stops. The above-described control is executed in response to control signals from the system controller 16.

Returning back to FIG. 1, reference numeral 20 represents a tomographic image data generator for obtaining tomographic image data at a desired slice plane of the patient 4 under the control of the system controller, using the measuring projection signals outputted from the X-ray detector 2. Reference numeral 21 represents an image display unit such as a CRT for displaying a tomogram at a slice plane under the control of the system controller using the tomographic image data.

The tomographic image data generator 20 is constructed of a data collection unit 22, an image reconstruction data generator 23, and an image reconstruction unit 24.

The data collection unit 22 is constructed of a data collection circuit 25 including pre-amplifiers, A/D converters, and the like, and a measuring projection data storage device 26 such as two-dimensional buffer memories. In response to signals from the system controller 16 synchronous with the rotation position of the X-ray source 1 and the motion position of the bed 3, the data collection circuit 25 sequentially samples the measuring projection signal outputted from each detector element 2a of the X-ray detector 2, to thereby output measuring projection data. The measuring projection data is stored in the measuring projection data storage device 26 while referencing each measuring projection data to the rotation position of the X-ray source 1, the motion position of the patient 4 (i.e., bed 3), and the position of a corresponding X-ray beam of the fan beam X-ray 11 obtained at the time of sampling each measuring projection data.

Figure 11A:
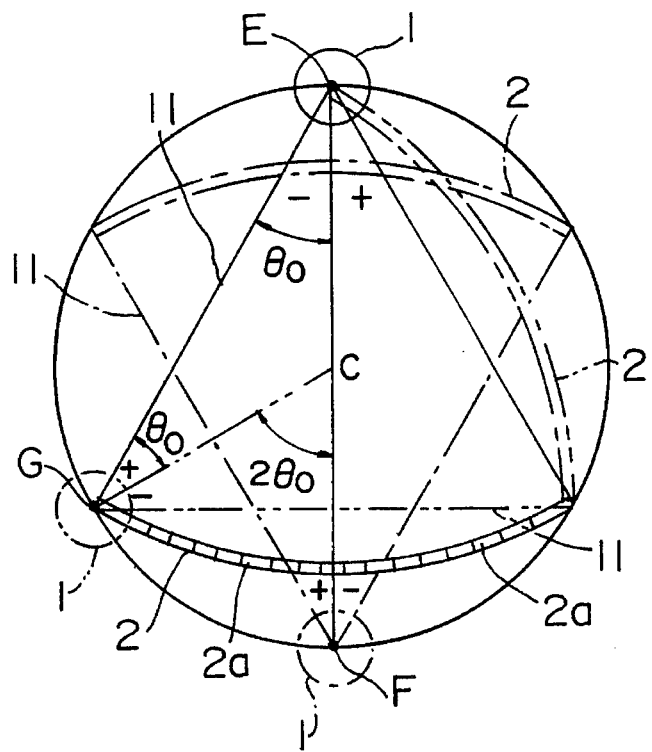
FIG. 11A is a front view showing the geometrical relation of the fan beam X-ray for explaining the counter projection data.
Figure 11B:
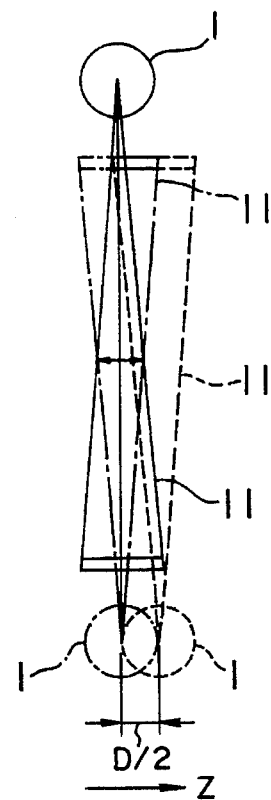
FIG. 11B is a side view showing the geometrical relation of the fan beam X-ray for explaining the counter projection data.

In this embodiment, as shown in FIG. 8A, each measuring projection data is sampled at p rotation positions having an equal angular pitch per one rotation (360 degrees) of the X-ray source 1, and at n rotation positions in total per several rotations of the X-ray source 1. For the convenience of description, a projection number i is defined as a sampling number allocated to each rotation position of the X-ray source 1 in the order of sampling the measuring projection data. Therefore, a relation $1 \leq j \leq n$ holds (where j and n are integers). Also for the convenience of description, the rotation position of the X-ray source 1 is given a name "projection angle", and the projection angle corresponding to the projection number j is expressed by $\beta(j)$ where $0° \leq \beta(j) < 360°$. Also for the convenience of description, it is assumed that the number of X-ray detector elements 2a is m, and a channel number i is defined as a number of each detector element 2a assigned in the order starting from the leftmost detector element 2a to the rightmost detector element 2a as viewed in connection with the positional relation between the X-ray source 1, X-ray detector 2, and fan beam X-ray 11 indicated by solid lines in FIG. 11A to be described later. A relation $1 \leq i \leq m$ holds (where i and m are integers). As described previously, each X-ray beam of the fan beam X-ray 11, which produces one of the measuring projection data, has a one-to-one correspondence with one particular detector element 2a so that the channel number i indicates the position of each X-ray beam of the fan beam X-ray 11. Referring to FIG. 11A, a beam angle is defined as an angle between each X-ray beam and a line EF passing through the center of the X-ray source 1 and its rotation center C, i.e., passing through the centers of the X-ray source 1 and the X-ray detector 2. The beam angle is 0° at the line EF, and takes a positive value on the left side of the line EF and a negative value on the right side as viewed in connection with the positional relation between the X-ray source 1, X-ray detector 2, and fan beam X-ray 11 indicated by solid lines in FIG. 11A. This beam angle also indicates the position of each X-ray beam of the fan beam X-ray 11. The beam angle corresponding to the channel number i is expressed as $\alpha(i)$. The detector elements 2a are disposed at an equal beam angle pitch $\Delta\alpha$ symmetrically with the line EF. For the convenience of description, in the drawings to follow, the position of the X-ray source 1 relative to the bed 3 is represented by a Z-axis as shown in FIG. 11B. The relative position of the X-ray source 1 is called a Z-axis position. The Z-axis position of the X-ray source 1 when sampling the measuring projection data is expressed by Zx.

Figure 6:
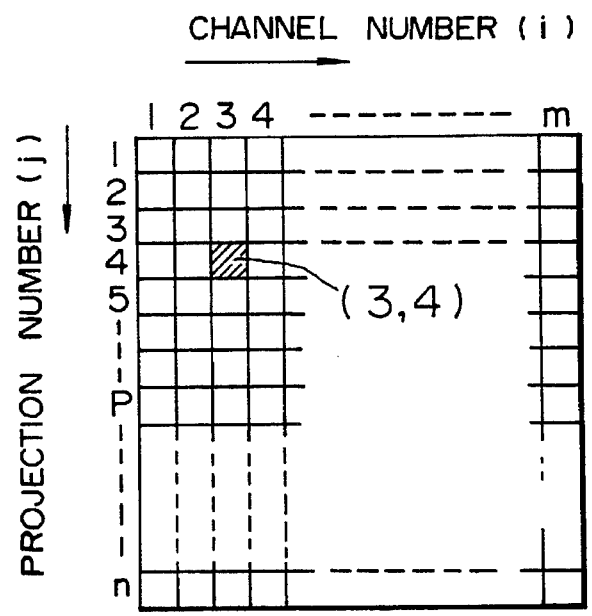
FIG. 6 shows the data structure of a projection data storage device.

As apparent from the foregoing description, the beam angle $\alpha(i)$ corresponds to the position of each X-ray beam of the fan beam X-ray 11, the projection angle $\beta(j)$ corresponds to the rotation position of the X-ray source 1, and Zx corresponds to the relative position of the patient 4 (i.e., bed 3). Therefore, each measuring projection data can be expressed by SR1($\alpha(i)$, $\beta(j)$, Zx) as a function of terms $\alpha(i)$, $\beta(j)$, and Zx. The term a (i) is definitely determined from the channel number i, $\beta(j)$ is definitely determined from the projection number j, and Zx is definitely determined from the projection number j. The reason why Zx is definitely determined from the projection number i is that the embodiment assumes a constant rotation speed of the X-ray source 1 and a constant motion speed of the bed 3. As a result, in this embodiment, each measuring projection data can be identified from the channel number i and projection number j. For this reason, each measuring projection data is stored in the measuring projection data storage device 26 using the channel number i and projection number j as its address as shown in FIG. 6.

The image reconstruction data generator 23 shown in FIG. 1 obtains image reconstruction data corresponding to each measuring projection data at each projection angle β(j), assuming that the projection data was obtained as if the patient 4 were stationary at a certain slice plane aligned with the rotation plane of the X-ray source 1.

The image reconstruction unit 24 shown in FIG. 1 obtains tomographic image data at a certain slice plane of the patient 4 from the image reconstruction data. As algorithms for reconstructing tomographic image data from measuring projection data, a direct back projection method, a re-ordering method, and other methods are known. With the direct back projection method, the measuring projection data itself is back-projected. With the re-ordering method, the measuring projection data is converted into data substantially the same as that obtained when projecting parallel X-ray beams, and the converted data is back-projected. The image reconstruction unit 24 may use any one of these algorithms. In this embodiment, the image reconstruction unit 24 is constructed of a filtration circuit 27, a back projector 28, and an image data storage device 29. The filtration circuit 27 performs known filtration of the image reconstruction data in order to remove image blur. The back projector 28 performs back projection and reconstruction of the image reconstruction data subjected to filtration by the filtration circuit 27 to obtain final tomographic image data. The image data storage device 29 stores tomographic image data obtained by the back projector 28.

Figure 7:
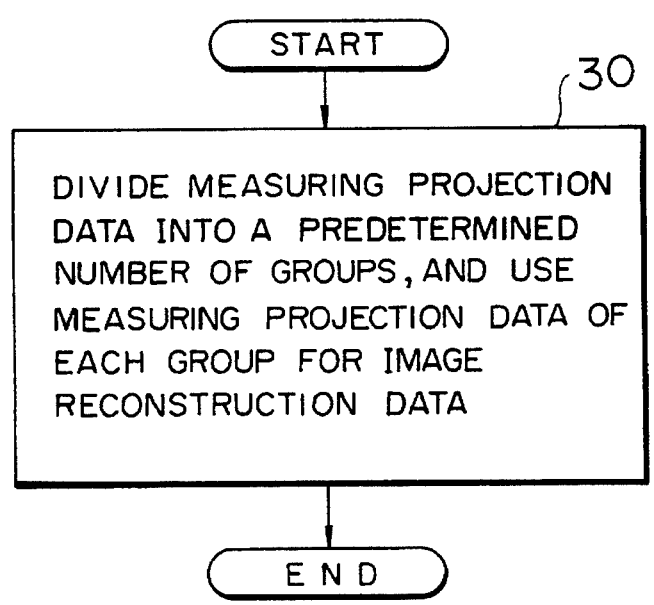
FIG. 7 is a flow chart showing the function of the image reconstruction data generator of the CT system according to an embodiment of the present invention.

In this embodiment, the image reconstruction data generator 23 has a function shown in the flow chart of FIG. 7. Specifically, at step 30 shown in FIG. 7, this generator 23 divides the measuring projection data into a plurality of groups each corresponding to one continuous 360° rotation angle range of the X-ray source 1, and uses the measuring projection data of each group as the image reconstruction data.

This function of the image reconstruction data generator 23 will be described specifically with reference to FIGS. 8A, 8B, and 8C. FIG. 8A shows a relation between rotation cycles of the X-ray source 1 and projection numbers j. FIG. 8B shows a locus S1 of the X-ray source 1 relative to the patient 4 in association with projection numbers. The Y-axis shown in FIG. 8B indicates the height of the X-ray source 1, and the Z-axis indicates the relative position of the X-ray source 1. The Y-axis has the same meaning in the drawings to follow. FIG. 8C shows the range of measuring projection data usable for the image reconstruction data in association with projection numbers j. More particularly, the image reconstruction data generator 23 groups the projection numbers j in units of p projection numbers as shown in FIG. 8A. The measuring projection data for each set of p projection numbers is used for the image reconstruction data at a slice plane of the patient 4, the slice plane being located at the center of the set in the Z-axis direction. For example, as shown in FIGS. 8A, 8B, and 8C, the measuring projection data for the projection numbers j from "1" to "p" is used for the image reconstruction data for an image A at the slice plane of the patient 4 at position ZA. Similarly, the measuring projection data for the projection numbers j from "p+1" to "2p" is used for the image reconstruction data for an image B at the slice plane of the patient 4 at position ZB.

According to the first embodiment of the present invention described so far, the measuring projection data obtained during one rotation of the X-ray source 1 is used directly for the image reconstruction data. Therefore, the X-ray source moves by a distance D in the X-axis direction during one rotation of the X-ray source 1, resulting in poor data consistencies. For example, in the case of the image reconstruction data for the image A, the data for the projection number "1" and the data for the projection number "p" have poor data consistencies. For this reason, there are relatively large artifacts. However, the first embodiment provides various advantages that the image reconstruction data generator 23 can process data in a simple manner and at a high processing speed.

Next, a CT system according to a second embodiment of the present invention will be described. The only difference between the second embodiment and the first embodiment is the function of the image reconstruction data generator 23. Therefore, only the function of the image reconstruction data generator 23 will be described while omitting the description of the other system components.

Figure 9:
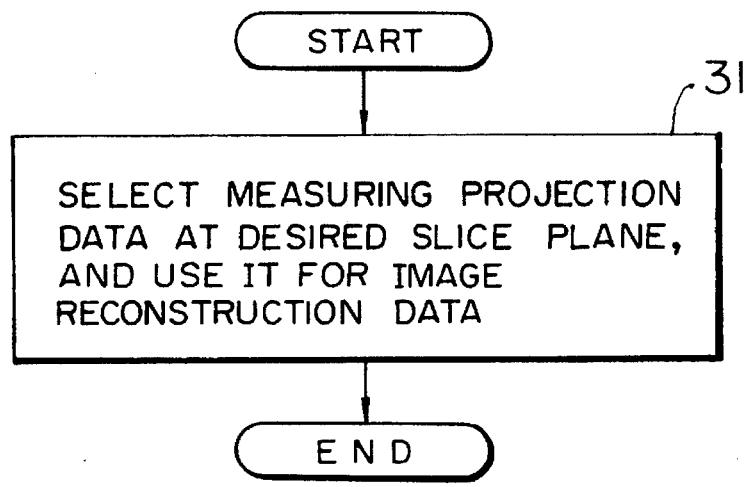
FIG. 9 is a flow chart showing the function of the image reconstruction data generator of the CT system according to another embodiment of the present invention.

In the second embodiment, the image reconstruction data generator 23 has a function shown in the flow chart of FIG. 9. Specifically, at step 31 shown in FIG. 9, this generator 23 uses for the image reconstruction data the measuring projection data within a predetermined rotation range which is shifted in accordance with a desired slice plane of the patient 4. The measuring projection data corresponds to the rotation positions of the X-ray source 1 within the continuous predetermined rotation range necessary for image reconstruction.

This function of the image reconstruction data generator 23 will be described specifically with reference to FIGS. 8A, 8B, and 8D. FIG. 8D shows the range of measuring projection data usable for the image reconstruction data in association with projection numbers j. More particularly, as shown in FIG. 8D, assuming that a desired slice plane of the patient 4 instructed from the system controller 16 of FIG. 1 is $Z_1$ in FIG. 8B, the measuring projection data for the projection numbers j from "1" to "p" within the Z-axis range from $Z_1-D/2$ to $Z_1+D/2$ (one continuous rotation range of 360° of the X-ray source 1) is used for the image reconstruction data for an image "1" at the slice plane of the patient 4 at the position $Z_1$. Similarly, as shown in FIG. 8D, assuming that a desired slice plane of the patient 4 is $Z_2$ shifted to the right from the position $Z_1$ by a distance (D/p) corresponding to one projection angle pitch Δβ, then the measuring projection data for the projection numbers j from "2" to "p+1" within the Z-axis range from $Z_2-D/2$ to $Z_2+D/2$ is used for the image reconstruction data for an image "2" at the slice plane of the patient 4 at the position $Z_2$. Similarly, as shown in FIG. 8D, assuming that a desired slice plane of the patient 4 is $Z_M$ shifted to the right from the position Z, by a distance (M–1) x (D/p), then the measuring projection data for the projection numbers j from "M" to "M+p–1" within the Z-axis range from $Z_M-D/2$ to $Z_M+D/2$ is used for the image reconstruction data for an image "M" at the slice plane of the patient 4 at the position $Z_M$. In the examples shown in FIG. 8D, the predetermined rotation range is set to 360°. This rotation range may be set smaller than 360°.

According to the second embodiment of the present invention described so far, although there are relatively large artifacts as in the first embodiment, the second embodiment provides various advantages that the image reconstruction data generator 23 can process data in a simple manner and at a high processing speed, and makes it possible to obtain tomographic image data at any optional slice plane of the patient 4.

Next, a CT system according to the third embodiment of the present invention will be described. The only difference between the third embodiment and the first embodiment is the function of the image reconstruction data generator 23. Therefore, only the function of the image reconstruction data generator 23 will be described while omitting the description of the other system components.

Figure 10:
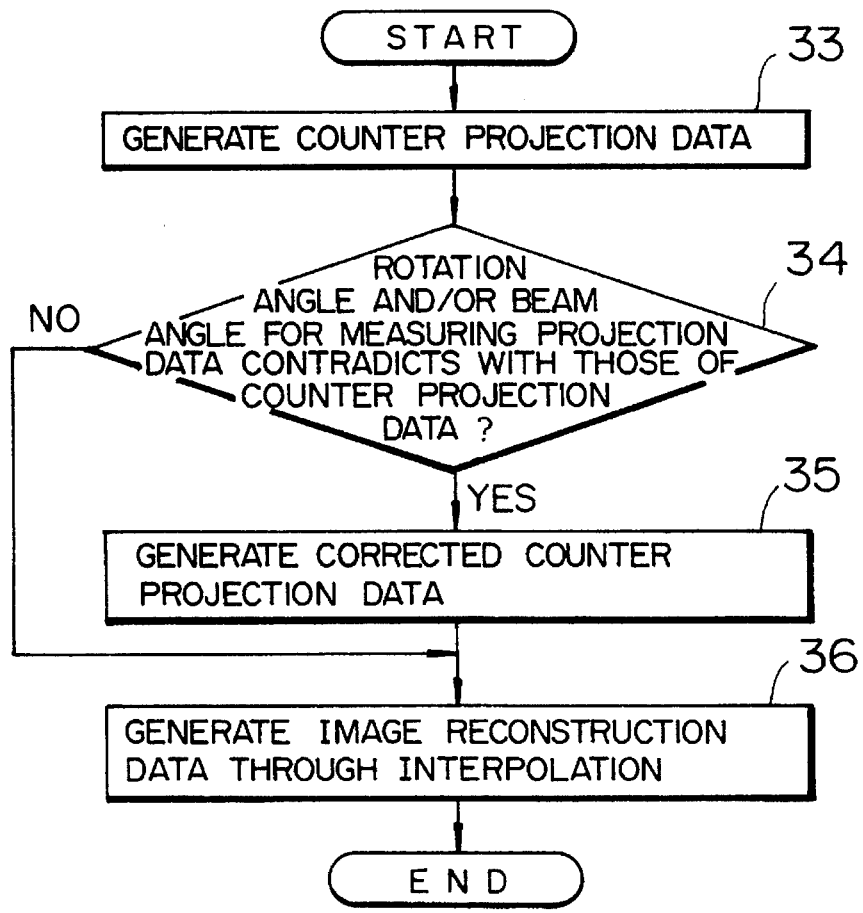
FIG. 10 is a flow chart showing the function of the image reconstruction data generator of the CT system according to a further embodiment of the present invention.

In the third embodiment, the image reconstruction data generator 23 has the function shown in the flow chart of FIG. 10.

First, at step 33 shown in FIG. 10, counter projection data is generated for each measuring projection data. Each counter projection data is substantially the same data as each measuring projection data, and is related to the rotation position of the X-ray source 1, the motion position of the patient 4, and the position of a virtual X-ray beam of the fan beam X-ray 11 when using a virtual X-ray beam having substantially the same path as, and a direction opposite to, those of the X-ray beam used for the measuring projection data. As is similar to the case where the measuring projection data is expressed by $SR1(\alpha(i), \beta(j), Zx)$, the counter projection data having the same data contents can be expressed by $SR2(\alpha(k), \beta(l), Zy)$. The term $\alpha(k)$ represents a beam angle of the virtual X-ray beam, $\beta(l)$ represents a projection angle providing the virtual X-ray beam, and Zy represents the Z-axis position of the X-ray source 1 providing the virtual X-ray beam.

The counter projection data will be described with reference to FIGS. 11A and 11B. FIG. 11A is a front view showing a geometry of the fan beam X-ray 11 for explaining the counter projection data, and FIG. 11b is a side view showing a geometry of the fan beam X-ray 11 explaining the counter projection data.

In FIG. 11A, it is assumed that a first counter projection data is obtained for an X-ray beam at a beam angle 0° and on a line EF passing through the rotation center of the X-ray source 1 at a point E. This X-ray beam is called a centered X-ray beam, and a detector element 2a receiving the centered X-ray beam is called a center channel detector element 2a. In the following description, the center channel detector element 2a is assumed to be actually present. However, the present invention is applicable even if the center channel detector 2a is not present. The rotation position of the X-ray source 1 is at the point F shifted by a 180° projection angle from the point E, which position provides a first virtual X-ray beam having the same path on the line EF as, and a direction opposite to, those of the centered X-ray beam from the X-ray source 1 at the point E. The beam angle of the first virtual X-ray beam is also 0°. As shown in FIG. 11B, the Z-axis position of the X-ray source 1 providing the first virtual X-ray beam is the same as that providing the first measuring projection data. The solid lines in FIG. 11B indicate the Z-axis position of the X-ray source 1 providing the first measuring projection data, the one-dot chain lines in FIG. 11B indicate the Z-axis position of the X-ray source 1 providing the first virtual X-ray beam, and the broken lines in FIG. 11B indicate the Z-axis position of the X-ray source 1 when it actually rotates to the point F.

Also in FIG. 11A, it is assumed that a second counter projection data is obtained for an actual X-ray beam at a beam angle $\theta_0$ (inclusive of + or − shown in FIG. 11A) and on a line EG from the X-ray source 1 at the point E. The rotation position of the X-ray source 1 is at the point G shifted by a projection angle of $180°-2\theta_0$ from the point E, which position provides a second virtual X-ray beam having the same path on the line EG as, and a direction opposite to, those of the actual X-ray beam. The beam angle of the second virtual X-ray beam is $-\theta_0$. The Z-axis position of the X-ray source 1 providing the second virtual X-ray beam is the same as that providing the second measuring projection data.

As will be appreciated from the foregoing description, the following relation holds between the terms $\alpha(i)$, $\beta(j)$, and Zx of the measuring projection data $SR1(\alpha(i), \beta(j), Zx)$ and the terms $\alpha(k)$, $\beta(l)$, and Zy of the counter projection data $SR2(\alpha(k), \beta(l), Zy)$ having the same data contents as the measuring projection data:

$$\alpha(k)=-\alpha(i) \quad (1)$$

$$\beta(l)=\beta(j)+(180°-2\alpha(i)) \quad (2)$$

$$Zy=Zx \quad (3)$$

As described previously, $1 \leq i \leq m$ (i and m are integers) and $1 \leq j \leq n$ (j and n are integers). The following relation is also satisfied:

$$Zx=Z_1+(D/p)*(j-1) \quad (4)$$

where D, p, and j have the meanings described previously, and $Z_1$ is the actual Z-axis position of the X-ray source 1 when the projection number j is "1".

As seen from the above description, each counter projection data having substantially the same data as each measuring projection data can be generated by relating it to the terms $\alpha(k)$, $\beta(l)$, and Zy satisfying the equations (1) to (3).

Figure 12:
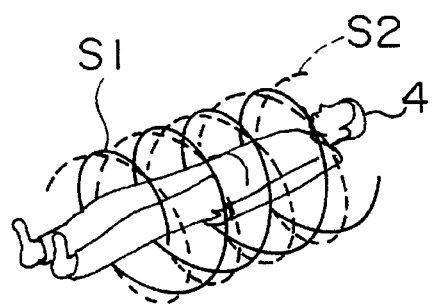
FIG. 12 is a perspective view showing the actual locus of the X-ray source and a virtual locus of the X-ray source for the counter projection data relative to a patient.

Now, consider the counter projection data for the centered X-ray beam at the center channel detector element 2a, which should have the same data as the corresponding measuring projection data. In this case, $\alpha(k)=0°$ from the equation (1) because $\alpha(i)=0°$, $\beta(l)=\beta(j)+180°$ from the equation (2), and $Zy=Zx$ from the equation (3). The following three conditions are met, namely, the measuring projection data and counter projection data for the center channel detector element 2a have the same data contents, the projection angles of the data differ by 180°, and the Z-axis positions for the data are the same. Accordingly, the locus S1 of the actual X-ray source 1 providing the measuring projection data and the locus S2 of the virtual X-ray source 1 providing the counter projection data for the center channel detector element 2a become as shown in FIGS. 12 and 13A. FIG. 12 is a perspective view showing the relation between the loci S1 and S2. FIG. 13A shows the relation between the loci S1 and S2 relative to the Y- and Z-axes. FIG. 13B shows the relation between the projection angle and the loci S1 and S2.

After completion of step 33 shown in FIG. 10, the control advances to step 34 of FIG. 10. At this step 34, it is checked whether there is any measuring projection data for which the rotation position of the X-ray source 1 and/or the beam angle related to the measuring projection data contradicts with the rotation position of the X-ray source 1 and/or the beam angle related to the corresponding counter projection data. Specifically, it is checked whether there is any $\alpha(i)$ contradicting with $\alpha(k)$, and whether there is any $\beta(j)$ contradicting with $\beta(l)$. Such contradiction occurs depending upon the beam angle pitch $\Delta\alpha$, a displacement amount of the detector element 2a from the line EF shown in FIG. 11A, and the projection angle pitch $\Delta\beta$. If no contradiction is found at the step 34, the control advances to step 36. If any contradiction is found, the control advances to step 35.

At the step 35, the counter projection data is corrected to obtain corrected counter projection data. The corrected counter projection data is obtained by the following two types of processing methods.

According to one processing method, the corrected counter projection data is obtained by replacing the terms $\alpha(k)$ and $\beta(l)$ of the counter projection data contradicting with the terms $\alpha(i)$ and $\beta(j)$ of the measuring projection data by the terms $\alpha(k)$ and $\beta(l)$ of another counter projection data near the contradicted counter projection data.

According to the other processing method, the corrected counter projection data is obtained by a process of interpolating a plurality of counter projection data related to the terms $\alpha(k)$ and $\beta(l)$ near the contradicted counter projection data. The corrected counter projection data is related to the new terms $\alpha(k)$ and $\beta(l)$ obtained through the interpolation process.

An example of the interpolation process will be described for the case where all terms $\alpha(i)$ have a correspondence with any one of the terms $\alpha(k)$, and there is a term $\beta(j)$ which contradicts with all terms $\beta(l)$. Zx is definitely determined by the projection number j as seen from the equation (4), and Zy is definitely determined by k and l to be described later. Accordingly, in the following description of a particular interpolation process, Zx and Zy are omitted to express the measuring projection data as $SR1(\alpha(i), \beta(j))$ and the counter projection data as $SR2(\alpha(k), \beta(l))$.

A value $\Delta J$ is defined as a value indicating the number of multiples of the projection angle pitch $\Delta\beta$ which becomes equal to $(180°-2\alpha(i))$ in the equation (2). The value $\Delta J$ is expressed by the following equation:

$$\Delta J=(180°-2\alpha(i))/\Delta\beta \tag{5}$$

Expressing the Gauss notation of the value $\Delta J$ by $\Delta j$, then:

$$\Delta j=[\Delta J] \tag{6}$$

which indicates the integer part of $\Delta J$. Expressing a difference between $\Delta j$ and $\Delta J$ by $\delta$, then:

$$\delta=\Delta J-\Delta j \tag{7}$$

The difference $\delta$ indicates the fraction part of $\Delta J$. From the equation (2), the following equation holds:

$$l=j+\Delta J=j+\Delta j+\delta \tag{8}$$

The corrected counter projection data $SR2'(\alpha(k), \beta(l))$ can be obtained by the interpolation process expressed by the following equation:

$$SR2'(\alpha(k), \beta(l))=(1-\delta)*SR1(\alpha(k), \beta(j+\Delta j))+ \\ \delta*SR1(\alpha(k), \beta(j+\Delta j+1)) \tag{9}$$

The l in the left side of the equation (9) is replaced by the value $j+\Delta J$ given by the equation (8). In the above equation (9), $k=m-i$ (m is the number of detector elements 2a). Although the notations $SR1(\alpha(k), \beta(j+\Delta j))$ and $SR1(\alpha(k), \beta(j+\Delta j+1))$ correspond to the measuring projection data, these data are the same as the two counter projection data on both sides of the contradicted counter projection data corresponding to the measuring projection data. The equation (9) represents a linear interpolation. The present invention may use other types of interpolation.

If the term $\beta(j)$ has a correspondence with any one of the terms $\beta(l)$ of the counter projection data, then $\delta=0$. In this case also, the counter projection data is obtained from the equation (9). Accordingly, if the interpolation process of the equation (9) is performed for all channel numbers (i=1 to m) and all projection numbers (j=1 to n), then automatically obtained are the counter projection data for the case where the term $\beta(j)$ has a correspondence with any one of the terms $\beta(l)$ and the corrected counter projection data for the case where the term $\beta(j)$ contradicts with all the terms $\beta(l)$. In other words, the interpolation process of the equation (9) automatically executes all the steps 33 to 35 shown in FIG. 10. For the convenience of description, $SR2'(\alpha(k), \beta(l))$ of the equation (9) is called arbitrated counter projection data.

In the above description, the Z-axis position is omitted in expressing each data. In the following, the Z-axis position Zy related to the arbitrated counter projection data $SR2'(\alpha(k), \beta(l))$ will be discussed. As described previously, $l=j+\Delta J$. From the foregoing description of the relation between the measuring projection data and counter projection data for the center channel detector element 2a, the Z-axis position for the counter projection data at the center channel detector element 2a (called center channel counter projection data) is clear. If a displacement amount $\Delta Z$ of the Z-axis position for a certain counter projection data at a certain projection angle, from the Z-axis position for the center channel counter projection data at that projection angle, is known, then the Z-axis position for the counter projection data can be determined. The displacement amount $\Delta Z$ of the arbitrated counter projection data $SR2'(\alpha(k), \beta(l))$ is expressed by the following equation:

$$\Delta Z = (j+\Delta j)*(D/p)-(j+\Delta jc)*(D/p) \\ = (\Delta j-\Delta jc)*(D/p) \tag{10}$$

As given by the equations (5) and (6), $\Delta j$ is expressed by:

$$\Delta j=[\Delta J]=[(180°-2\alpha(i))/\Delta\beta] \tag{11}$$

$\Delta jc$ in the equation (10) represents $\Delta j$ for the center channel counter projection data. Substituting $\alpha(i)=0°$ in the equation (11), $\Delta jc$ can be obtained as:

$$\Delta jc=[180°/\Delta\beta] \tag{12}$$

From the equations (10) to (12), the displacement amount Z is definitely determined by i and j. Accordingly, the X-axis position Zy for the arbitrated counter projection data $SR2'(\alpha(k), \beta(l))$ is definitely determined by k and l. In FIG. 13C, a broken line shows the relation between the Z-axis position and the beam angle of the arbitrated counter projection data (or simply counter projection data) at a certain projection angle, and a solid line shows the relation between the Z-axis position and the beam angle of the measuring projection data at that projection angle. In the case of the measuring projection data, the Z-axis position is constant and independent of the beam angle at the same projection angle, as seen from the equation (4).

In the above-described operation of obtaining corrected counter projection data, it has been assumed that all the terms $\alpha(i)$ have a correspondence with any one of the terms $\alpha(k)$. If there is a term $a(i)$ having no correspondence with any one of the terms $\alpha(k)$, an interpolation process similar to the above-described process is executed between channels or beam angles.

At step 36 shown in FIG. 10, the measuring projection data and counter projection data or corrected counter projection data at the arbitrated projection angles and beam angles are subjected to an interpolation process to obtain image reconstruction data substantially the same as the projection data which would be obtained at each projection angle if each desired slice plane of the patient 4 were aligned with the rotation plane 17.

An example of such an interpolation process for the measuring projection data $SR1(\alpha(i), \beta(j), Zx)$ and arbitrated counter projection data $SR2'(\alpha(k), \beta(l), Zy)$ will be described with reference to FIGS. 13A and 13B. By the time of this process, the term $\alpha(k)$ already has a corresponding $\alpha(i)$ and the term $\beta(l)$ already has a corresponding $\beta(j)$ as discussed above. For the convenience of description, the representation for the arbitrated counter projection data is changed to $SR2'(\alpha(i), \beta(j), Zy)$. This change necessarily results in an unsatisfied relation of $SR1(\alpha(i), \beta(j), Zx) = SR2'(\alpha(i), \beta(j), Zy)$.

The Z-axis position of a desired slice plane of the patient 4 is assumed to be Zs in FIG. 13A. Zs is notified from the system controller 16 shown in FIG. 1. The image reconstruction data at the desired slice plane is expressed as $R(\alpha(i), \beta(j))$. For the convenience of description, the range extending from the position Zs at the slice plane in opposite directions on the Z-axis for a distance of D/2, i.e., the range from Zs−D/2 to Zs+D/2, is defined as an interpolation range. The measuring projection data SR1 and arbitrated counter projection data SR2' at the arbitrated projection angles and beam angles are subject to an interpolation process. Specifically, such an interpolation process is carried out using the measuring projection data SR1 related to the Z-axis position within the interpolation range (the measuring projection data SR1 obtained when the X-ray source 1 actually moves from a point G1 to a point G2 shown in FIG. 13A), and the arbitrated counter projection data SR2' related to the Z-axis position within or near the interpolation range (the arbitrated counter projection data SR2' at the center channel detector element 2a, i.e., at the condition of $\alpha(i)=0°$, obtained when the X-ray source 1 virtually moves from a point G3 to a point G4 shown in FIG. 13A). This interpolation process is carried out in accordance with a ratio of the distance from the Z-axis position for the measuring projection data SR1 to Zs, to the distance from the Z-axis position for the arbitrated counter projection data SR2' to Zs. For example, the image reconstruction data R at Zs or at $\alpha(i)=0°$ and at $\beta(j)=\beta7$ shown in FIGS. 13A and 13B is obtained by the interpolation process using the measuring projection data SR1 at $\beta(j)=\beta7$ and at $\alpha(i)=0°$ and the arbitrated counter projection data SR2' at $\beta(j)=62\ 7$ and at $\alpha(i)=0°$ in accordance with the ratio of the Z-axis distance rx between points G6 and G7 to the Z-axis distance (D/2−rx) between points G5 and G7.

The above-described process is expressed by the following equation:

$$R(\alpha(i), \beta(j))=W*SR1(\alpha(i), \beta(j), Zx)+(1-W)*SR2'(\alpha(i), \beta(j), Zy) \quad (13)$$

where W is expressed as:

$$W=(\Delta Z+rx)/(\Delta Z+(D/2)) \quad (14)$$

In the equation (14), $\Delta Z$ is expressed by the equation (10). The process expressed by the equation (13) is performed for all projection numbers j and all channel numbers (i=1 to m) included within the range from Zs−D/2 to Zs+D/2 to thereby obtain all corresponding image reconstruction data. As seen from FIGS. 13A and 13B, rx is determined by $\beta(j)$.

In the foregoing description, the interpolation range has been set to D or one rotation of the X-ray source 1. The range D may be narrowed depending upon the type of image reconstruction. Furthermore, the interpolation range has been set relative to the center Z-axis position Zs. The interpolation range may be set shifted from the center Z-axis position Zs. As seen from FIGS. 13A and 13B, if the maximum value of $\Delta Z$ is large, the equation (14) represents not interpolation but extrapolation. The term "interpolation" used in this specification includes not only interpolation but also extrapolation. If the maximum value of $\Delta Z$ is relatively small, $\Delta Z$ may be neglected and set to 0 in the equation (14).

According to the third embodiment of the present invention described above, the image reconstruction data generator 23 generates image reconstruction data substantially the same as would be obtained if each projection data at each rotation position of the X-ray source 1 were obtained by stopping the bed 3 with a desired slice plane of the patient 4 being aligned with the rotation plane 17 of the X-ray source 1. Therefore, artifacts can be considerably reduced. Furthermore, in obtaining each image reconstruction data substantially the same as obtained from each projection data, not only the measuring projection data but also the counter projection data is used. Therefore, the Z-axis distances between positions of the X-ray source 1 and a desired slice plane (in the example shown in FIG. 13A, rx and (D/2−rx)) corresponding to two projection data used for Z-axis interpolation can be shortened, thereby providing tomographic image data of high precision.

Next, a CT system according to the fourth embodiment of the present invention will be described. The only difference between the third embodiment and the first embodiment is the function of the image reconstruction data generator 23. Therefore, only the function of the image reconstruction data generator 23 will be described while omitting the description of the other system components.

In the fourth embodiment, the image reconstruction data generator 23 generates image reconstruction data for a desired slice plane of the patient 4 as if the bed 3 were smoothly moved in such a manner that while the X-ray source 1 rotates once, the rotation plane 17 of the X-ray source 1 moves forward from the anterior position of the slice area of the patient 4 to the posterior position thereof, and then moves back to the original position.

The image reconstruction data generator 23 of the fourth embodiment has a function described by the flow chart shown in FIG. 15. The contents of steps 40 and 41 shown in FIG. 15 will be described below with reference to FIGS. 16A, 16B, and 16C. FIG. 16A shows the actual locus S1 of the X-ray source and the virtual locus S3 thereof to be described later. The Y- and Z-axes have the same meanings described previously. FIG. 16B shows the relation between the loci S1 and S3 and the projection angle. FIG. 16C shows the loci S1 and S3 with the vertical axis representing the projection angle instead of the Y-axis. The Z-axis positions at points G10 to G19 shown in FIG. 16C are represented by Z10 to Z19, respectively. For the convenience of description, the Z-axis position of a desired slice plane of the patient 4 is assumed to be Zs shown in FIG. 16A. Zs is notified from the system controller 16 shown in FIG. 1. The image reconstruction data for a desired slice plane is represented by $R(\alpha(i), \beta(j))$.

First, at the step 40 shown in FIG. 15, of the measuring projection data $SR1(\alpha(i), \beta(j), Zx)$, used for the image reconstruction data $R(\alpha(i), \beta(j))$ is the measuring projection data having Zx within the range H2 from Zs−D/4 to Zs+D/4 narrower than the range H1 corresponding to one rotation of the X-ray source 1. This process is expressed by the following equation:

$$R(\alpha(i), \beta(j))=SR1(\alpha(i), \beta(j), Zx) \quad (15)$$

where $Zs-D/4 \leq Zx \leq Zs+D/4$. In the example shown in FIGS. 16A, 16B, and 16C, $0° < \beta(j) \leq 180°$.

Next, at the step 41 shown in FIG. 15, the image reconstruction data $R(\alpha(i), \beta(j))$ for the projection angle $\beta(j)$ within the range H1 excepting the range H2, i.e., the range from 180° to 360° in the example shown in FIGS. 16A, 16B, and 16C, is obtained through an interpolation process of two measuring projection data $SR1(\alpha(i), \beta(j), Zx)$ at the projection angle $\beta(j)$ nearer to Zs. For example, consider the sine wave virtual locus S3 of the X-ray source 1 indicated by a dotted line in FIGS. 16A and 16C. In this case, the image reconstruction data $R(\alpha(i), \beta12)$ at a point G12 ($\beta(j)=\beta12$, $Zx=Z12$) is obtained from the following equation, using the measuring projection data $SR1(\alpha(i), \beta12, Z13)$ at a point G13 ($\beta(j)=\beta12, Zx=Z13$) and the measuring projection data $SR1(\alpha(i), \beta12, Z14)$ at a point G14 ($\beta(j)=\beta12, Zx=Z14$):

$$R(\alpha(i), \beta12)=\{a1*SR1(\alpha(i), \beta12, Z13)+b1*SR1(\alpha(i), \beta12, Z14)\}/(a1+b1) \quad (16)$$

where $$a1=Z14-Z12 \quad (17)$$

$$b1=Z12-Z13 \quad (18)$$

$$a1+b1=D \quad (19)$$

The image reconstruction data $R(\alpha(i), \beta15)$ at a point G15 ($\beta(j)=\beta15, Zx=Z15$) is obtained from the following equation, using the measuring projection data $SR1(\alpha(i), \beta15, Z16)$ at a point G16 ($\beta(j)=\beta15, Zx=Z16$) and the measuring projection data $SR1(\alpha(i), \beta15, Z17)$ at a point G17 ($\beta(j)=\beta15, Zx=Z17$):

$$R(\alpha(i), \beta15)=\{a2*SR1(\alpha(i), \beta15, Z16)+b2*SR1(\alpha(i), \beta15, Z17)\}/(a2+b2) \quad (20)$$

where $$a2=Z17-Z14 \quad (21)$$

$$b2=Z15-Z16 \quad (22)$$

$$a2+b2=D \quad (23)$$

At the step 41, the above operation is performed for each point on the locus S3.

In the example described above and shown in FIGS. 15, 16A, 16B, and 16C, the image reconstruction data is obtained as if the X-ray source 1 were moved from the point G10 to G11 on the actual locus S1 and moved back to the point G10 on the virtual locus S3 via the points G12 and G15.

In the example described above and shown in FIGS. 15, 16A, 16B, and 16C, although the equations (16) and (20) use linear interpolation, any other interpolation methods may be used. Furthermore, the range H2 has been set to D/2 in the above example. This range may be set wider or narrower. Also, although the range H2 is centered at Zs, this range H2 may be shifted right and left relative to Zs in FIG. 16A. Still further, the sine wave virtual locus S3 has been used in the above example. This locus S3 may be any other curve including a straight line part.

Figure 14I:
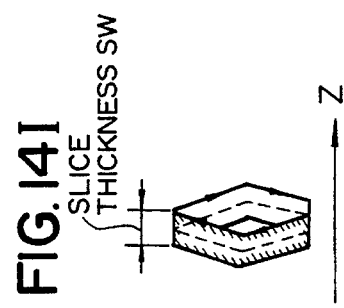
FIG. 14I shows another virtual measuring state by the fan beam X-ray.
Figure 14D:
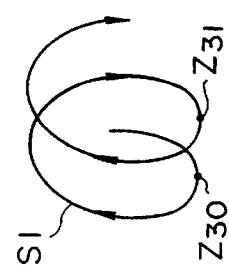
FIG. 14D shows an actual locus of the X-ray source for spiral scanning.
Figure 14A:
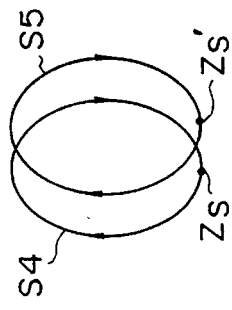
FIG. 14A shows an actual locus of the X-ray source for a conventional stationary patient.
Figures 14E, 14G:
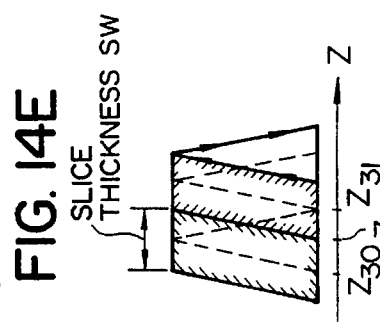
FIG. 14E shows the actual measuring state by a fan beam X-ray for the spiral scanning.
FIG. 14G shows the virtual measuring state by the fan beam X-ray.
Figure 14B:
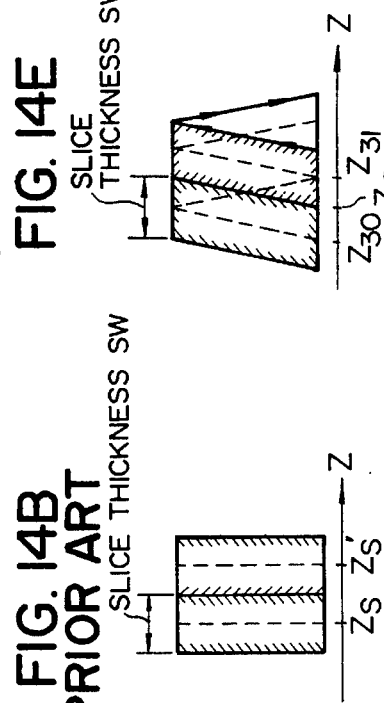
FIG. 14B shows the actual measuring state of the conventional stationary patient by the fan beam X-ray.
Figure 14H:
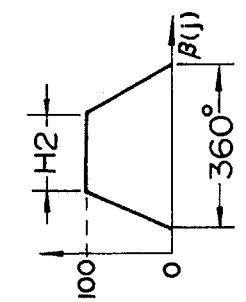
FIG. 14H shows the contribution factor of the measuring projection data to the image reconstruction data at each projection angle, wherein the data substantially the same as obtained in the virtual measuring state shown in FIG. 14G per se is used for the image reconstruction data.
Figure 14F:
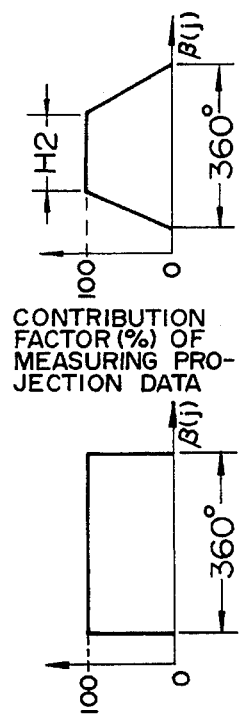
FIG. 14F shows the contribution factor of the measuring projection data to the image reconstruction data at each projection angle, wherein the measuring projection data in the measuring state shown in FIG. 14E per se is used for the image reconstruction data.
Figure 14C:
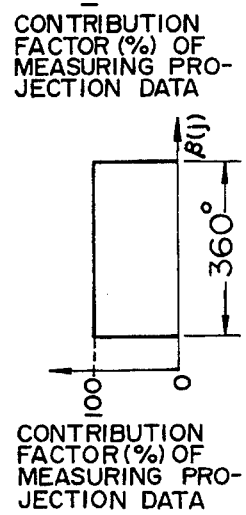
FIG. 14C shows the contribution factor of the measuring projection data to the image reconstruction data at each projection angle, wherein the measuring projection data in the measuring state shown in FIG. 14B per se is used for the image reconstruction data.

In the example described above and shown in FIGS. 15, 16A, 16B, and 16C, the virtual measuring state of the patient 4 by the fan beam X-ray 11 is conceptually shown in FIG. 14G, and the contribution factor of the measuring projection data to the image reconstruction data becomes as shown in FIG. 14H. The meanings of FIGS. 14G and 14H will be clarified by comparison to FIGS. 14A to 14F. FIG. 14A is a perspective view showing actual loci S4 and S5 of an X-ray source for a conventional stationary patient. FIG. 14B is a conceptual diagram showing the measuring state of the stationary patient with a fan beam X-ray as viewed in the Z-axis direction. In the example shown in FIGS. 14A and 14B, the Z-axis positions of the loci S4 and S5 coincide with the Z-axis positions Zs and Zs' of desired slice planes. The distance between Zs and Zs' is set to the slice thickness SW of the fan beam X-ray. As seen from FIGS. 14A and 14B, in the case of the conventional stationary patient, the measuring range (projection range) of the fan beam X-ray does not shift in the Z-axis direction. Since the measuring projection data at Zs and at each projection angle per se is used for the image reconstruction data, the contribution of the measuring projection data to the image reconstruction data is 100% as shown in FIG. 14C at each projection angle of the measuring projection data. Since the measuring range of the fan beam X-ray does not shift in the Z-axis direction, artifacts are small. FIG. 14D is a perspective view showing an actual locus S1 of the X-ray source 1 according to the spiral scanning of the present invention. FIG. 14E is a conceptual diagram showing the measuring state of a patient 4 with a fan beam X-ray 11 in the spiral scanning. In the example shown in FIGS. 14D and 14E, D=SW. As seen from FIGS. 14D and 14E, in the spiral scanning, the measuring range (projection range) of the fan beam X-ray 11 will shift from Z30 to Z31 in the Z-axis direction while the X-ray source 1 rotates once. In the first and second embodiments described above, the measuring projection data per se obtained at each projection angle while the X-ray source 1 rotates once from Z30 to Z31 is used for the image reconstruction data. Accordingly, the contribution factor of the measuring projection data to the image reconstruction data is 100% as shown in FIG. 14F at each projection angle of the measuring projection data. In the first and second embodiments, artifacts are relatively large, because the measuring projection data per se obtained at each projection angle during one rotation of the X-ray source 1 is used for the image reconstruction data in spite of the fact that the measuring range (projection range) by the fan beam X-ray 11 shifts in the Z-axis direction during one rotation of the X-ray source 1. However, in the third embodiment, the virtual measuring state (measuring state for the image reconstruction data) of the patient by the fan beam X-ray 11 becomes the same as FIG. 14A, because the measuring projection data substantially the same as that obtained when the X-ray source 1 is moved in the manner shown in FIG. 14A is used for the image reconstruction data. Accordingly, in the third embodiment, artifacts can be considerably reduced. In the fourth embodiment described above and shown in FIGS. 15, 16A, 16B, and 16C, the measuring projection data is used for part of the image reconstruction data, and the measuring projection data virtually obtained while moving the X-ray source 1 in the above-described manner is used for the remaining part of the image reconstruction data. Accordingly, the virtual measuring state (measuring state for the image reconstruction data) of the patient 4 by the fan beam X-ray 11 becomes as shown in FIG. 14G. FIG. 14G shows the virtual measuring state with two desired slice planes corresponding to two Z-axis positions Zs and Zs', respectively. In FIG. 14G, the distance between Zs and Zs' is set to the slice thickness of the fan beam X-ray. In this example, as shown in FIG. 14H, the contribution factor of the measuring projection data to the image reconstruction data changes with the projection angle for the measuring projection data. The range H2 with the contribution factor of 100% shown in FIG. 14H corresponds to the range H2 shown in FIG. 16A. Although the relative measuring range (projection range) of the fan beam X-ray 11 shifts in the Z-axis direction during one rotation of the X-ray source 1, it smoothly returns to the original Z-axis position after one rotation of the X-ray source 1. Accordingly, the difference between image reconstruction data at adjacent projection angles becomes small. Artifacts can be considerably reduced correspondingly as compared with the first and second embodiments, although they are somewhat larger than those of the third embodiment. Furthermore, the measuring projection data per se is used for part of the image reconstruction data. Therefore, as compared to the third embodiment, the fourth embodiment described above and shown in FIGS. 15, 16A, 16B, and 16C is simpler with respect to generation of the image reconstruction data, and has a high processing speed. Dotted lines in FIGS. 14B, 14E, and 14G indicate the center of the slice thickness SW. In the fourth embodiment, the virtual measuring state of the patient 4 by the fan beam X-ray 11 may take a configuration other than a perfect loop, such as shown in FIG. 14I.

One example of the operation to be executed by the image reconstruction data generator 14 of the fourth embodiment has been described above in connection with FIGS. 15, 16A, 16B, and 16C.

Next, another example of the operation to be executed by the image reconstruction data generator 14 of the fourth embodiment will be described.

Figure 17:
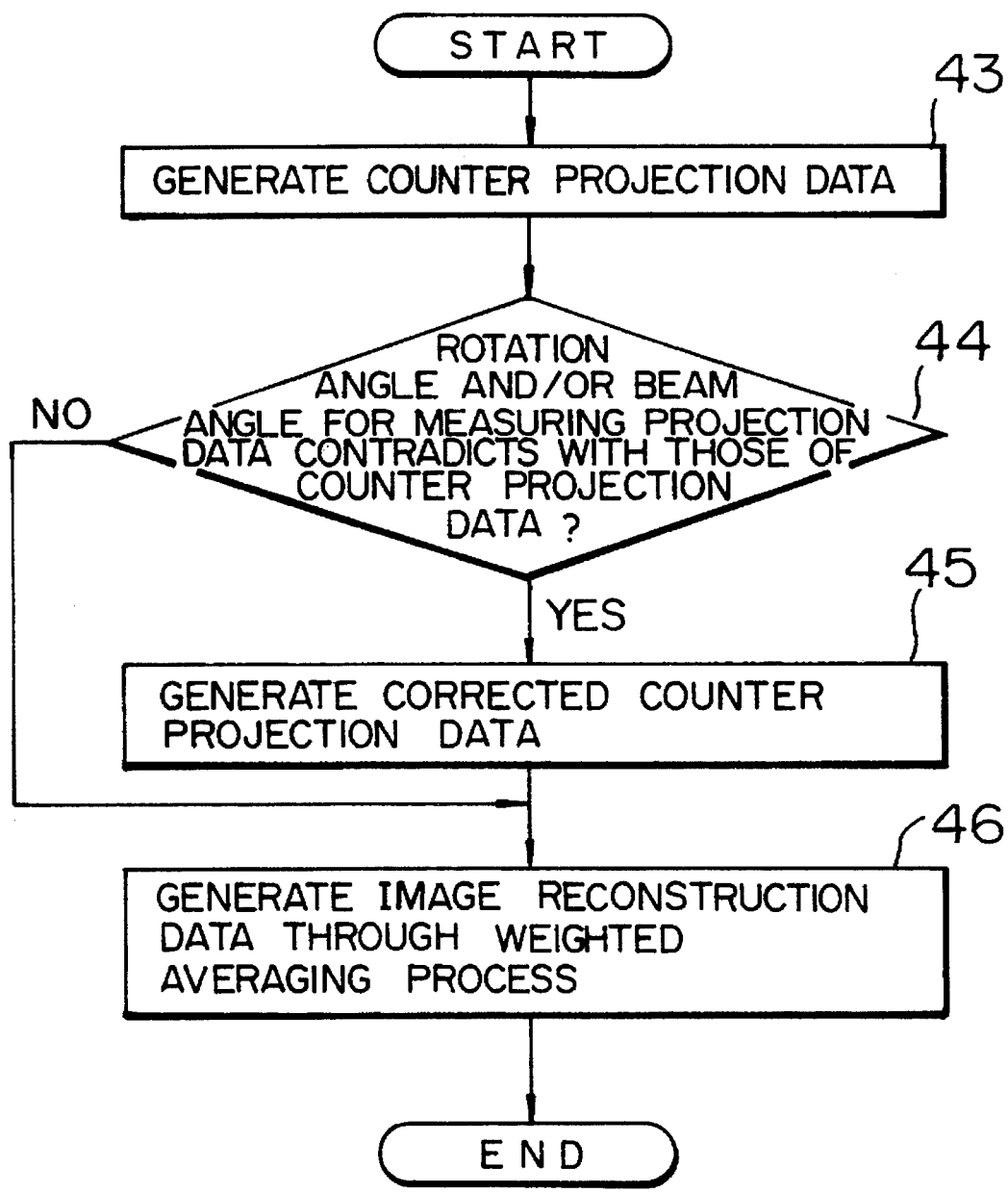
FIG. 17 is a flow chart showing the function of the image reconstruction data generator of the CT system according to another embodiment of the present invention.

FIG. 17 is a flow chart showing the operation of the image reconstruction data generator 23. Steps 43 to 45 in FIG. 17 are the same as the steps 33 to 35 in FIG. 10, so the description thereof is omitted.

At step 46 shown in FIG. 17, by means of a weighted averaging process at the arbitrated projection angles and beam angles, the image reconstruction data generator 23 generates image reconstruction data for a desired slice plane of the patient 4 as if the bed 3 were smoothly moved in such a manner that while the X-ray source 1 rotates once, the rotation plane 17 of the X-ray source 1 moves forward from the anterior position of the slice area of the patient 4 to the posterior position thereof, and then moves back to the original position.

An example of the weighted averaging process for the measuring projection data $SR1(\alpha(i), \beta(j), Zx)$ and arbitrated counter projection data $SR2'(\alpha(i), \beta(j), Zx)$ will be described with reference to FIGS. 18A to 18F. FIG. 18A shows an actual locus S1 of the X-ray source 1 providing the measuring projection data, and a virtual locus S2 of the X-ray source 1 providing counter projection data at the center channel detector element 2a. FIG. 18B shows the relation between the loci S1 and S2 and the projection angle. FIG. 18C shows the relation between the weight coefficients Wx for the measuring projection data $SR1(\alpha(i), \beta(j), Zx)$ and the loci S1 and S2. FIG. 18D shows the relation between the weight coefficients Wy for the arbitrated counter projection data $SR2'(\alpha(i), \beta(j), Zx)$ and the loci S1 and S2. The Z-axis shown in FIG. 18D represents the Z-axis position at $\alpha(i)=0°$. FIG. 18E shows the weight coefficients Wx with the horizontal axis representing the projection angle. FIG. 18F shows the weight coefficients Wy with the horizontal axis representing the projection angle. The Z-axis positions at points G25 to G28 in FIG. 18A are represented by Z25 to Z28, respectively. The weight coefficients at points Z25 and Z27 are represented by W25 and W27, respectively. The weight coefficients at points Z26 and Z28 are represented by W26 and W28, respectively.

The Z-axis position of a desired slice plane of the patient 4 is assumed to be Zs in FIG. 18A. Zs is notified from the system controller 16 shown in FIG. 1. The image reconstruction data at the desired slice plane is expressed as $R(\alpha(i), \beta(j))$. For the convenience of description, the range from Zs−D/2 to Zs+D/2 at the desired slice plane is defined as a weighted averaging range. The measuring projection data SR1 and arbitrated counter projection data SR2' at the arbitrated projection angles and beam angles are subject to a weighted averaging process. Specifically, such a weighted averaging process is carried out using the measuring projection data SR1 related to the Z-axis position within the weighted averaging range (the measuring projection data SR1 obtained when the X-ray source 1 actually moves from a point G21 to a point G22 shown in FIG. 18A), and the arbitrated counter projection data SR2' related to the Z-axis position within or near the weighted averaging range (the arbitrated counter projection data SR2' at the center channel detector element 2a, i.e., at the condition of $\alpha(i)=0°$, obtained when the X-ray source 1 virtually moves from a point G23 to a point G24 shown in FIG. 18A). As shown in FIGS. 18E and 18F, the weight coefficients Wx and Wy are determined so as to satisfy the following equation:

$$Wx+Wy=1 \qquad (24)$$

As shown in FIGS. 18C and 18E, Wx is set to a value which takes a value nearer to "1" the more the projection angle for the measuring projection data becomes near to the projection angle βs for Zs, and takes a value nearer to "0" the more it becomes far from the projection angle βs. In this embodiment, Wy is set to a value not related to the displacement amount ΔAZ, i.e., independent of $\alpha(i)$. Specifically, referring to FIGS. 18A to 18D, the image reconstruction data $R(0°, \beta25)$ at $\alpha(i)=0°$ and $\beta(j)=\beta25$ is obtained from the following equation using the measuring projection data $SR1(0°, \beta25, Z25)$ at a point G25 ($\alpha(i)=0°$, $\beta(j)=\beta25$, Zx=Z25) and the arbitrated counter projection data $SR2'(0°, \beta25, Z26)$ at a point G26 ($\alpha(i)=0°$, $\beta(j)=\beta25$, Zx=Z26):

$$R(0°, \beta25)=W25*SR1(0°, \beta25\ Z25)+W26*SR2'(0°, \beta25\ Z26) \qquad (25)$$

where the following equation holds:

$$W25+W26=1 \qquad (26)$$

The image reconstruction data $R(0°, \beta27)$ at $\alpha(i)=0°$ and $\beta(j)=\beta27$ is obtained from the following equation using the measuring projection data $SR1(0°, \beta27, Z27)$ at a point G27 ($\alpha(i)=0°$, $\beta(j)=\beta27$, Zx=Z27) and the arbitrated counter projection data $SR2'(0°, \beta27, Z28)$ at a point G28 ($\alpha(i)=0°$, $\beta(j)=\beta27$, Zx=Z28):

$$R(0°, \beta27)=W27*SR1(0°, \beta27\ Z27)+W28*SR2'(0°, \beta27\ Z28) \qquad (27)$$

where the following equation holds:

$$W27+W28=1 \qquad (28)$$

The above-described process is expressed by the following equation:

$$R(\alpha(i), \beta(j))=Wx*SR1(\alpha(i), \beta(j), Zx)+Wy*SR2'(\alpha(i), \beta(j), Zy) \qquad (29)$$

The process expressed by the equation (13) is performed for all projection numbers j and all channel numbers (i=1 to m) included within the range from Zs−D/2 to Zs+D/2 to thereby obtain all corresponding image reconstruction data.

In the foregoing description, the weighted averaging range has been set to D or one rotation of the X-ray source 1. The range D may be narrowed depending upon the type of image reconstruction. Furthermore, the weighted averaging range has been set relative to the center Z-axis position Zs. The weighted averaging range may be set shifted from the center Z-axis position Zs.

Also in the example described above and shown in FIGS. 17 and 18A to 18F, the virtual measuring state of the patient 4 by the fan beam X-ray 11 becomes similar to that shown in FIG. 14G, thereby making small the difference between image reconstruction data at adjacent projection angles and reducing artifacts.

Next, another embodiment of the CT system according to the present invention will be described. The only difference between this embodiment and the first embodiment is the function of the image reconstruction data generator 23. Accordingly, only the function of the image reconstruction generator 23 will be described while omitting the description of the other system components.

In this embodiment, the image reconstruction data generator 23 generates the image reconstruction data $R(\alpha(i), \beta(j))$ for a desired slice plane of the patient at the Z-axis position Zs using the following equation:

$$R(\alpha(i), \beta(j))=W3*SR1(\alpha(i), \beta(j), Zx)+W4*SRa(\alpha(i)) \quad (30)$$

Figure 19A:
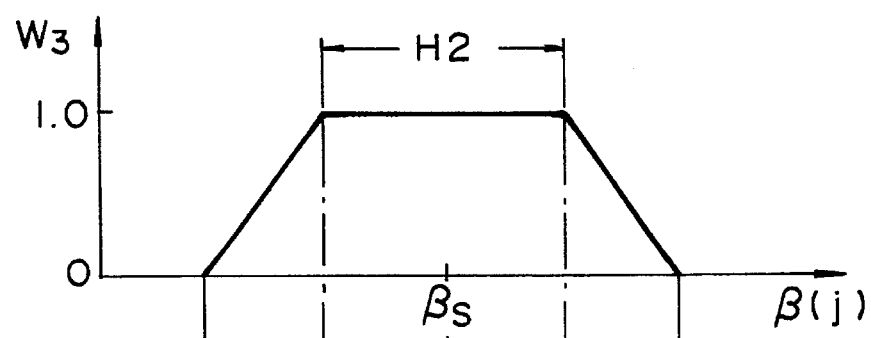
FIGS. 19A and 19B show weight coefficients used in another embodiment of the present invention.
Figure 19B:
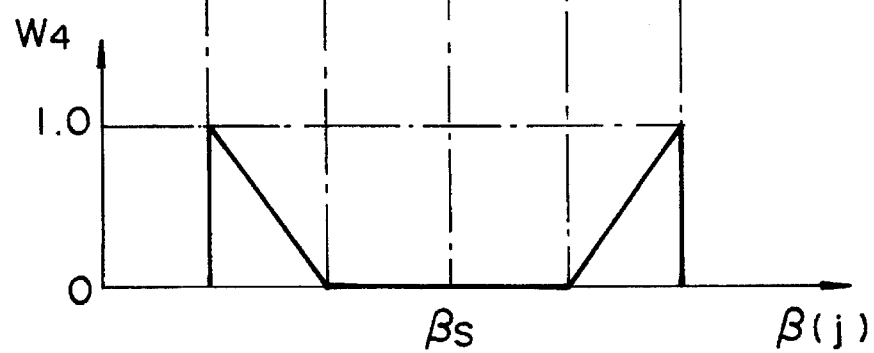

$SRa(\alpha(i))$ in the equation (30) is an average value between the measuring projection data SR1 at $Zx=Zs-D/2$ and the counter projection data SR2 at $Zx=Zs+D/2$. W3 and W4 are weight coefficients and are set to values shown in FIGS. 19A and 19B. In FIGS. 19A and 19B, $\beta s$ is the projection angle for Zs. The relation between W3 and W4 is expressed by:

$$W3+W4=1 \quad (31)$$

The process expressed by the equation (30) is performed for all projection numbers i and all channel numbers (i=1 to m) included within the range from Zs−D/2 to Zs+D/2 to thereby obtain all corresponding image reconstruction data.

In the foregoing description, as shown in FIGS. 19A and 19B, the range H2 within which the weight coefficients W3 are set to "1" covers 180° (corresponding to D/2). However, this range may be set as desired.

Also in this embodiment, the difference can be made small between image reconstruction data at adjacent projection angles, and artifacts can be reduced.

Although the preferred embodiments have been described above, the present invention is not limited to only such embodiments. Although a CT system of a rotate/rotate type has been used in each embodiment, the present invention is applicable to other types of CT systems such as a CT system of a stationary/rotate type with detector elements being mounted circumferentially on the gantry.

We claim:

1. A computed tomography system comprising:

a radiation source for irradiating a fan beam radiation ray to an object, said radiation source continuously rotating within a predetermined rotation plane, said fan beam radiation ray expanding in a fan shape substantially within said rotation plane;

moving means for continuously moving said object in a predetermined direction such that said rotation plane continuously traverses different parts of said object while said radiation source rotates;

radiation detector means mounted on the opposite side of said object relative to said radiation source, said radiation detector means including a plurality of detector elements disposed so as to receive radiation of said fan beam radiation ray, each said detector element being responsive to a radiation beam which is part of said fan beam radiation ray transmitted through said object and outputting a measuring projection signal corresponding to the intensity of said radiation beam;

data collecting means for collecting measuring projection data for each said radiation beam at each of a plurality of predetermined rotation positions of said radiation source in accordance with said measuring projection signal while relating each said measuring projection data to the rotation position of said radiation source, the position of said object moved by said moving means, and the position of said radiation beam of said fan beam radiation ray;

image reconstruction data generator means for generating image reconstruction data for a desired slice plane of said object in accordance with said measuring projection data, said image reconstruction data being obtained from said measuring projection data obtained at each said rotation position of said radiation source; and image reconstructing means for obtaining tomographic image data of said object for said desired slice plane in accordance with said image reconstruction data;

wherein said image reconstruction data generator means includes selecting means for selecting said measuring projection data within a predetermined continuous rotation range of said radiation source necessary for image reconstruction, and for using said selected measuring projection data for said image reconstruction data, said predetermined continuous rotation range being shifted by an amount as small as an amount corresponding to one rotation position of said radiation source in accordance with a position of said desired slice plane of said object.

2. A computed tomography system according to claim 1, wherein said image reconstructing means includes means for obtaining tomographic image data of said object by assuming that said image reconstruction data originates from measuring projection data obtained at each said rotation position of said radiation source at said desired slice plane.

3. A computed tomography system according to claim 1, wherein said selecting means includes means for selecting said measuring projection data within a predetermined rotation range of 360°.

4. A computed tomography system comprising:

a radiation source for irradiating a fan beam radiation ray to an object, said radiation source continuously rotating within a predetermined rotation plane, said fan beam radiation ray expanding in a fan shape substantially within said rotation plane;

moving means for continuously moving said object in a predetermined direction such that said rotation plane continuously traverses different parts of said object while said radiation source rotates;

radiation detector means mounted on the opposite side of said object relative to said radiation source, said radiation detector means including a plurality of detector elements disposed so as to receive radiation of said fan beam radiation ray, each said detector element being responsive to a radiation beam which is part of said fan beam radiation ray transmitted through said object and outputting a measuring projection signal corresponding to the intensity of said radiation beam;

data collecting means for collecting measuring projection data for each said radiation beam at each of a plurality of predetermined rotation positions of said radiation source in accordance with said measuring projection signal while relating each said measuring projection data to the rotation position of said radiation source, the position of said object moved by said moving means, and the position of said radiation beam of said fan beam radiation ray;

image reconstruction data generator means for generating image reconstruction data for a desired slice plane of said object in accordance with said measuring projection data, said image reconstruction data being obtained from said measuring projection data obtained at each said rotation position of said radiation source; and image reconstructing means for obtaining tomographic image data of said object for said desired slice plane in accordance with said image reconstruction data;

wherein said image reconstruction data generator means includes:

counter projection data generator means for generating counter projection data for each said measuring projection data, said counter projection data being substantially the same as a corresponding one of said measuring projection data and being related to the rotation position of said radiation source, the position of said object moved by said moving means, and the position of a virtual radiation beam of said fan beam radiation ray, said virtual radiation beam having substantially the same path as, and a direction opposite to, said radiation beam for said corresponding one of said measuring projection data; and first data generator means for obtaining said image reconstruction data in accordance with said measuring projection data and said counter projection data;

wherein said first data generator means includes:

first corrected counter projection data generator means for obtaining first corrected counter projection data from said counter projection data when a rotation position and/or a beam angle related to said measuring projection data contradicts with a rotation position and/or a beam angle related to said counter projection data by replacing said rotation position and said beam angle related to said counter projection data corresponding to said contradicting measuring projection data with a rotation position and a beam angle related to counter projection data near said rotation position and said beam angle related to said counter projection data corresponding to said contradicting measuring projection data; and second data generator means for generating said image reconstruction data using said measuring projection data and said counter projection data or said first corrected counter projection data, said counter projection data being related to a rotation position and a beam angle not contradicting with a rotation position and a beam angle of any one of said measuring projection data.

5. A computed tomography system according to claim 4, wherein said second data generator means includes means for obtaining said image reconstruction data through interpolation by using said measuring projection data and said counter projection data or said first corrected counter projection data having related thereto substantially the same rotation positions and beam angles.

6. A computed tomography system according to claim 4, wherein said second data generator means includes means for obtaining said image reconstruction data through interpolation by using said measuring projection data and said counter projection data or said first corrected counter projection data, said measuring projection data being related to a position of said object within an object motion range inclusive of a position of said object with said rotation plane of said radiation source being aligned with said desired slice plane, said object motion range corresponding substantially to one rotation of said radiation source, and said counter projection data being related to positions of said object within or near to said object motion range.

7. A computed tomography system according to claim 4, wherein said second data generator means includes means for obtaining said image reconstruction data through interpolation by using said measuring projection data and said counter projection data or said first corrected counter projection data having related thereto substantially the same rotation positions and beam angles, said interpolation being performed in accordance with substantially a same ratio as a ratio of a first distance to a second distance, said first distance being defined by a distance between a position of said object related to said measuring projection data and a position of said object with said rotation plane of said radiation source being aligned with said desired slice plane, and said second distance being defined by a distance between a position of said object related to said counter projection data or said first corrected counter projection data and the position of said object with said rotation plane of said radiation source being aligned with said desired slice plane.

* * * * *

UNITED STATES PATENT AND TRADEMARK OFFICE
CERTIFICATE OF CORRECTION

PATENT NO. : 5,454,019
DATED : September 26, 1995
INVENTOR(S) : Migita et al.

It is certified that error appears in the above-identified patent and that said Letters Patent is hereby corrected as shown below:

On the title page of the patent, in item [73] (Assignee), delete "Hitachi, Ltd., Tokyo, Japan" insert --Hitachi Medical Corporation, Tokyo, Japan--.

Signed and Sealed this

Second Day of May, 2000

Attest:

Q. TODD DICKINSON

Attesting Officer

Director of Patents and Trademarks